(12) United States Patent
Nohara et al.

(10) Patent No.: US 10,793,307 B2
(45) Date of Patent: Oct. 6, 2020

(54) FILL-FINISH PROCESS FOR PEPTIDE SOLUTIONS

(71) Applicant: 3-D MATRIX, LTD., Tokyo (JP)

(72) Inventors: Masahiro Nohara, Tokyo (JP); Yuya Hasegawa, Saitama (JP)

(73) Assignee: 3-D Matrix, Ltd., Tokyo (JP)

( * ) Notice: Subject to any disclaimer, the term of this patent is extended or adjusted under 35 U.S.C. 154(b) by 404 days.

(21) Appl. No.: 14/413,156

(22) PCT Filed: Jul. 3, 2013

(86) PCT No.: PCT/US2013/049327
§ 371 (c)(1),
(2) Date: Jan. 6, 2015

(87) PCT Pub. No.: WO2014/008400
PCT Pub. Date: Jan. 9, 2014

(65) Prior Publication Data
US 2015/0197359 A1 Jul. 16, 2015

Related U.S. Application Data

(60) Provisional application No. 61/668,688, filed on Jul. 6, 2012.

(51) Int. Cl.
| | | |
|---|---|---|
| *C07K 1/34* | (2006.01) |
| *C07K 1/36* | (2006.01) |
| *C07K 7/08* | (2006.01) |
| *B65B 55/12* | (2006.01) |
| *B65B 3/00* | (2006.01) |
| *B65B 55/04* | (2006.01) |
| *B65B 63/00* | (2006.01) |
| *C07K 5/103* | (2006.01) |
| *C07K 5/11* | (2006.01) |
| *A61K 38/00* | (2006.01) |

(52) U.S. Cl.
CPC ............ *B65B 55/12* (2013.01); *B65B 3/003* (2013.01); *B65B 55/04* (2013.01); *B65B 63/00* (2013.01); *C07K 1/34* (2013.01); *C07K 1/36* (2013.01); *C07K 7/08* (2013.01); *A61K 38/00* (2013.01); *C07K 5/101* (2013.01); *C07K 5/1019* (2013.01)

(58) Field of Classification Search
CPC .......... B65B 55/12; A61K 38/00; C07K 1/14; C07K 1/34; C07K 1/36; C07K 7/08
See application file for complete search history.

(56) References Cited

U.S. PATENT DOCUMENTS

| | | | |
|---|---|---|---|
| 4,466,641 A | 8/1984 | Heilman et al. |
| 4,582,640 A | 4/1986 | Smestad et al. |
| 4,642,117 A | 2/1987 | Nguyen et al. |
| 4,947,840 A | 8/1990 | Yannas et al. |
| 5,110,604 A | 5/1992 | Chu et al. |
| 5,126,141 A | 6/1992 | Henry |
| 5,236,903 A | 8/1993 | Saiki et al. |
| 5,292,514 A | 3/1994 | Capecchi et al. |
| 5,510,102 A | 4/1996 | Cochrum |
| 5,527,610 A | 6/1996 | Urry |
| 5,550,187 A | 8/1996 | Rhee et al. |
| 5,670,483 A | 9/1997 | Zhang et al. |
| 5,747,452 A | 5/1998 | Ruoslahti et al. |
| 5,773,577 A | 6/1998 | Cappello |
| 5,955,343 A | 9/1999 | Holmes et al. |
| 6,046,160 A | 4/2000 | Obi-Tabot |
| 6,224,893 B1 | 5/2001 | Langer et al. |
| 6,228,324 B1 * | 5/2001 | Hasegawa ............... A61L 2/208 422/30 |
| 6,280,474 B1 | 8/2001 | Cassidy et al. |
| 6,548,630 B1 | 4/2003 | Zhang et al. |
| 6,730,298 B2 | 5/2004 | Griffith-Cima et al. |
| 6,800,481 B1 | 10/2004 | Holmes et al. |
| 7,098,028 B2 | 8/2006 | Holmes et al. |
| 7,449,180 B2 | 11/2008 | Kisiday et al. |
| 7,713,923 B2 | 5/2010 | Genove et al. |
| 7,846,891 B2 | 12/2010 | Ellis-Behnke et al. |
| 8,022,178 B2 | 9/2011 | Horii et al. |
| 9,012,404 B2 | 4/2015 | Spirio et al. |
| 9,084,837 B2 | 7/2015 | Ellis-Behnke et al. |
| 9,162,005 B2 | 10/2015 | Ellis-Behnke et al. |
| 9,327,010 B2 | 5/2016 | Ellis-Behnke et al. |
| 9,339,476 B2 | 5/2016 | Norchi et al. |

(Continued)

FOREIGN PATENT DOCUMENTS

| | | |
|---|---|---|
| CA | 2572964 A1 | 2/2006 |
| CA | 2618184 A1 | 12/2006 |

(Continued)

OTHER PUBLICATIONS

Horii, et al, Biological Designer Self-Assembling Peptide Nanofiber Scaffolds Significantly Enhance Osteoblast Proliferation, Differentiation and 3-D Migration, PLoS ONE, Feb. 2007, Issue 2.*

(Continued)

*Primary Examiner* — Jeffrey E. Russel
(74) *Attorney, Agent, or Firm* — IP Supra, PLLC; Constantine Linnik; Robert Kelley Roth

(57) ABSTRACT

The enclosed disclosure describes, among other things, a method including the steps of a first deaerating step in which a mixture comprising peptides is deaerated by lowering the pressure, filtering the mixture through a sterilizing filter; and a second deaerating step, in which the filtrate is deaerated by vibration and lowering the pressure.

24 Claims, No Drawings

Specification includes a Sequence Listing.

(56) References Cited

U.S. PATENT DOCUMENTS

| | | |
|---|---|---|
| 9,364,513 B2 | 6/2016 | Ellis-Behnke et al. |
| 9,415,084 B2 | 8/2016 | Ellis-Behnke et al. |
| 9,439,941 B2 | 9/2016 | Ellis-Behnke et al. |
| 9,724,448 B2 | 8/2017 | Kobayashi et al. |
| 10,245,299 B2 | 4/2019 | Mehta et al. |
| 10,369,237 B2 | 8/2019 | Gil et al. |
| 2002/0160471 A1 | 10/2002 | Kisiday et al. |
| 2003/0069177 A1 | 4/2003 | Dubaquie et al. |
| 2003/0166846 A1 | 9/2003 | Rothstein et al. |
| 2004/0081588 A1* | 4/2004 | Hammerstedt .......... A01N 1/02 422/550 |
| 2004/0204561 A1 | 10/2004 | Ellison |
| 2004/0242469 A1 | 12/2004 | Lee et al. |
| 2005/0181973 A1 | 8/2005 | Genove et al. |
| 2005/0287186 A1 | 12/2005 | Ellis-Behnke et al. |
| 2006/0084607 A1 | 4/2006 | Spirio et al. |
| 2006/0148703 A1 | 7/2006 | Lee et al. |
| 2006/0293243 A1 | 12/2006 | Puri et al. |
| 2007/0128175 A1 | 6/2007 | Ozbas et al. |
| 2007/0186567 A1* | 8/2007 | Gasteyer ................. F26B 5/06 62/66 |
| 2007/0190603 A1 | 8/2007 | Holmes et al. |
| 2008/0032934 A1 | 2/2008 | Ellis-Behnke et al. |
| 2008/0091233 A1 | 4/2008 | Ellis-Behnke et al. |
| 2009/0053103 A1 | 2/2009 | Mortimer et al. |
| 2009/0111734 A1 | 4/2009 | Ellis-Behnke et al. |
| 2009/0162437 A1 | 6/2009 | Horii et al. |
| 2009/0169598 A1 | 7/2009 | Crutcher |
| 2009/0252749 A1* | 10/2009 | Leister ............. C07K 14/70521 424/178.1 |
| 2010/0096328 A1* | 4/2010 | Hamasaki ............ B01D 65/102 210/638 |
| 2010/0143504 A1 | 6/2010 | Spirio et al. |
| 2010/0311640 A1 | 12/2010 | Genove et al. |
| 2011/0002880 A1 | 1/2011 | Takamura et al. |
| 2011/0201541 A1* | 8/2011 | Takamura ............... A61K 38/16 514/1.1 |
| 2012/0010140 A1 | 1/2012 | Ellis-Behnke et al. |
| 2012/0058066 A1 | 3/2012 | Nagai et al. |
| 2012/0070427 A1 | 3/2012 | Kaplan et al. |
| 2013/0281547 A1 | 10/2013 | Spirio et al. |
| 2013/0296239 A1 | 11/2013 | Takamura et al. |
| 2014/0038909 A1 | 2/2014 | Takamura et al. |
| 2014/0286888 A1 | 9/2014 | Nagai et al. |
| 2014/0329914 A1 | 11/2014 | Kobayashi et al. |
| 2015/0105336 A1 | 4/2015 | Takamura et al. |
| 2015/0258166 A1 | 9/2015 | Spirio et al. |
| 2015/0290329 A1 | 10/2015 | Heilshorn et al. |
| 2015/0328279 A1 | 11/2015 | Ellis-Behnke et al. |
| 2016/0000966 A1 | 1/2016 | Kobayashi et al. |
| 2016/0015855 A1 | 1/2016 | Nohara et al. |
| 2016/0030628 A1 | 2/2016 | Kobayashi |
| 2016/0213906 A1 | 7/2016 | Horita et al. |
| 2016/0287744 A1 | 10/2016 | Kobayashi et al. |
| 2016/0317607 A1 | 11/2016 | Spirio et al. |
| 2016/0362451 A1 | 12/2016 | Gil et al. |
| 2017/0072008 A1 | 3/2017 | Mehta et al. |
| 2017/0128622 A1 | 5/2017 | Spirio et al. |
| 2017/0173105 A1 | 6/2017 | Mehta et al. |
| 2017/0173221 A1 | 6/2017 | Mehta et al. |
| 2017/0202986 A1 | 7/2017 | Gil et al. |
| 2018/0369452 A1 | 12/2018 | Maki et al. |
| 2019/0111165 A1 | 4/2019 | Gil et al. |

FOREIGN PATENT DOCUMENTS

| | | | |
|---|---|---|---|
| CN | 101198350 A | 6/2008 | |
| CN | 101378773 A | 3/2009 | |
| CN | 101514225 A | 8/2009 | |
| EP | 2146667 A2 | 1/2010 | |
| EP | 2345433 A1 | 7/2011 | |
| EP | 2823830 A1 | 1/2015 | |
| EP | 3031466 A1 | 6/2016 | |
| JP | 2005-515796 A | 6/2005 | |
| JP | 2005-263631 A | 9/2005 | |
| JP | 2007-105186 A | 4/2007 | |
| JP | 2007-521009 A | 8/2007 | |
| JP | 2007-526232 A | 9/2007 | |
| JP | 2008-505919 A | 2/2008 | |
| JP | 2008-539257 A | 11/2008 | |
| JP | 2008-546689 A | 12/2008 | |
| JP | 2009-011341 A | 1/2009 | |
| JP | 2009-535338 A | 10/2009 | |
| JP | 2010-280719 A | 12/2010 | |
| JP | 2012-082180 A | 4/2012 | |
| JP | 5255274 B2 | 8/2013 | |
| JP | 2014-527543 A | 10/2014 | |
| JP | 5730828 B2 | 6/2015 | |
| JP | 5922749 B2 | 5/2016 | |
| WO | WO-94/17811 A1 | 8/1994 | |
| WO | WO-1996/040033 A1 | 12/1996 | |
| WO | WO-1997/037694 A1 | 10/1997 | |
| WO | WO-99/53019 A1 | 10/1999 | |
| WO | WO-00/01238 A1 | 1/2000 | |
| WO | WO-2002/022072 A2 | 3/2002 | |
| WO | WO-02/062969 A2 | 8/2002 | |
| WO | WO-2002/058749 A2 | 8/2002 | |
| WO | WO-2002/062961 A2 | 8/2002 | |
| WO | WO-03/084980 A2 | 10/2003 | |
| WO | WO-03/096972 A2 | 11/2003 | |
| WO | WO-2004/007532 A2 | 1/2004 | |
| WO | WO-2005/001076 A2 | 1/2005 | |
| WO | WO-2005/014615 A2 | 2/2005 | |
| WO | WO-2005/082399 A2 | 9/2005 | |
| WO | WO-2006/014570 A2 | 2/2006 | |
| WO | WO-2006/116524 A1 | 11/2006 | |
| WO | WO-2006/138023 A1 | 12/2006 | |
| WO | WO-2007/076032 A2 | 7/2007 | |
| WO | WO-2007/142757 A2 | 12/2007 | |
| WO | WO-2008/039483 A2 | 4/2008 | |
| WO | WO-2008/073392 A2 | 6/2008 | |
| WO | WO-2008/073395 A2 | 6/2008 | |
| WO | WO 2008077155 A1 * | 6/2008 | ........... A61L 2/0094 |
| WO | WO-2008/113030 A2 | 9/2008 | |
| WO | WO-2008/127607 A2 | 10/2008 | |
| WO | WO-2008/134544 A1 | 11/2008 | |
| WO | WO-2009/072556 A1 | 6/2009 | |
| WO | WO-2010/041636 A1 | 4/2010 | |
| WO | WO-2012/008967 A1 | 1/2012 | |
| WO | WO-2013/030673 A2 | 3/2013 | |
| WO | WO-2013/133413 A1 | 9/2013 | |
| WO | WO-2014/008400 A2 | 1/2014 | |
| WO | WO-2014/076660 A1 | 5/2014 | |
| WO | WO-2014/136081 A1 | 9/2014 | |
| WO | WO-2014/141143 A1 | 9/2014 | |
| WO | WO-2014/141160 A1 | 9/2014 | |
| WO | WO-2015/027203 A2 | 2/2015 | |
| WO | WO-2015/030063 A1 | 3/2015 | |
| WO | WO-2015/136370 A2 | 9/2015 | |
| WO | WO-2015/138473 A1 | 9/2015 | |
| WO | WO-2015/138475 A1 | 9/2015 | |
| WO | WO-2015/138478 A1 | 9/2015 | |
| WO | WO-2015/138514 A1 | 9/2015 | |
| WO | WO-2017/120092 A1 | 7/2017 | |

OTHER PUBLICATIONS

Whatman Product Guide, 1997.*
Thermo Scientific, MaxQ 2000 Open-Air Platform Shaker, 2010.*
Mimotopes, A Guide to Handling and Storing Peptides, PU3-004-1, Feb. 20, 2011, Date established via Internet achieve http://www.mimotopes.com/files/editor_upload/File/PeptidesAndAntibodies/PU3004-1Handling-and-Storing-Peptides.PDF.*
Baumfalk, Filter Integrity Testing in the Pharmaceutical Process Environment, BiopharmInternational.com, Jun. 1, 2006.*
Horii, et al. (Biological Designer Self-Assembling Peptide Nanofiber Scaffolds Significantly Enhance Osteoblast Proliferation, Differentiation and 3-D Migration, PLoS ONE, Feb. 2007, Issue 2, of record (Year: 2007).*
Kumuda (Functionalized scaffolds of shorter self-assembling peptides containing MMP-2 cleavable motif promote fibroblast proliferation

(56) References Cited

OTHER PUBLICATIONS and significantly accelerate 3-D cell migration independent of scaffold stiffness, Soft Matter 2010) (Year: 2010).*
Hielscher Ultrasonics Technology (2008, downloaded from https://www.hielscher.com/degassing_01.htm) (Year: 2008).*
Horii, et al. (Biological Designer Self-Assembling Peptide Nanofiber Scaffolds Significantly Enhance Osteoblast Proliferation, Differentiation and 3-D Migration, PLoS ONE, Feb. 2007, Issue 2, previously cited). (Year: 2007).*
Sun-Sri (Sample preparation, 2009, date established by internet achieve May 22, 2019) (Year: 2009).*
Rogers (Steam: Uses and Challenges for Device Sterilization, Sterilization 2006) (Year: 2006).*
Pall Corp (Year: 2019).*
Aguado, B. A. et al., Improving Viability of Stem Cells During Syringe Needle Flow Through the Design of Hydrogel Cell Carriers, Tissue Eng Part A., 18(7-8): 806-815. (2012).
Anderson, J. M. et al., Modulating the Gelation Properties of Self-Assembling Peptide Amphiphiles, ACS Nano., 3(11): 3447-3454 (2009).
Deshpande, A. P., Techniques in oscillatory shear rheology. SERC School-cum-Symposium on Rheology of Complex Fluids Jan. 4-9, 2010, Indian Institute of Technology Madras, Chennai, India https://physics.iitm.ac.in/-compflu/Lect-notes/abhijit.pdf, accessed online on Jan. 23, 2020, 23 pages (2010).
Gao, J., Self-assembly and Gelation Properties of Novel Peptides for Biomedical Applications, Thesis submitted to University of Manchester for the degree of Doctor in Philosophy, Accessed online at https://www.escholar.manchester.ac.uk/api/datastream?publication Pid=uk-ac-man-scw:200520&datastreamId=Fu LL-TEXT. PDF on Jan. 14, 2020. 180 pages. (Year: 2013).
Gasiorowski, J. Z., and Collier, J. H., Directed Intermixing in Multicomponent Self-Assembling Biomaterials, Biomacromolecules, 12: 3549-3559 (2011).
Guvendiren, M. et al., Shear-thinning hydrogels for biomedical applications, Soft Matter, 8: 260-272 (2012).
Hsu, B. B. et al, Clotting Mimicry from Robust Hemostatic Bandages Based on Self-Assembling Peptides, ACS Nano, 9(9): 9394-9406 (2015).
Meng, H. et al, The effect of a self-assembling peptide nanofiber scaffold (peptide) when used as a wound dressing for the treatment of deep second degree burns in rats, J. Biomed. Mater Res. B. Appl. Biomater., 89(2): 379-91 (2009).
Paradís-Bas, M. et al, RADA-16: A Tough Peptide—Strategies for Synthesis and Purification, Eur. J. Org. Chem., 5871-5878 (2013).
PuraStat® Synthetic Surgical Hemostatic Agent, Product Information, Nanotechnology Products Database, registration date Mar. 30, 2017, retrieved from <<https://product.statnano.com/product/8558>>, accessed on Oct. 11, 2019.
Taghavi, L, et al, Evaluation of the hemocompatability of RADA 16-1 peptide, J. Biomat. App.. 32(8): 1024-1031 (2018).
Vader, D. and Wyss, H., Introduction to Rheology, retrieved from <<http://weitzlab.seas.harvard.edu/files/weitzlab/files/introductiontorheology2.pdf>>, accessed online on Jan. 22, 2020, 31 pages (2020).
Xu, F. F. et al, Comparison between self-assembling peptide nanofiber scaffold (SAPNS) and fibrin sealant in neurosurgical hemostasis, Clin. Transl. Sci., 8(5): 490-4 (2015).
3-D Matrix Japan, Ltd. Company Profile Power Point, 32 pages, May 2005 (with English translation).
3-D Matrix Japan, Ltd., Products and FAQs, with English Translation, 14 pages. URL: http:/web.archive.org [Retrieved Oct. 21, 2016].
3D Matrix Japan, Company, Technology, Products, Technology, FAQs, Publication, Company, News, Contact, no English translation, 17 pages. URL: http://www.3d-matrix.co.jp/cm02.html [Retrieved Feb. 25, 2005].
3D Matrix Japan, Product Features, with English translation, 2 pages. URL: http://web.archive.org/web/20050416044014/http://www.3d-matrix.eo.jp/pr03.html [Retrieved Feb. 20, 2013].
3D Matrix Japan, Product List, with English translation, 2 pages. URL: http://web.archive.org/web/20050416043834/http://www.3d-matrix.co.jp/pr02.html [Retrieved Aug. 1, 2013].
3D Matrix Japan, Products, with English translation, 2 pages. URL: http://web.archive.org/web/20050415004502/http://www.3d-matrix.eo.jp/pr01.html [Retreived Feb. 20, 2013].
3D-Matrix Japan, Products, FAQs, 8 pages, dispatched Sep. 20, 2011 [English translation].
Abukawa, H. et al, Reconstructing Mandibular Defects Using Autologous Tissue-Engineered Tooth and Bone Constructs, J. Oral Maxillofac. Surg., 67(2):335-347 (2009).
Allen, P. et al, Type I collagen, fibrin and PuraMatrix matrices provide permissive environments for human endothelial and mesenchymal progenitor cells to form neovascular networks, J. Tissue Eng. Regen Med., 5(4):e74-86 (2011).
Altman, M. et al., Conformational behavior of ionic self-complementary peptides, Protein Sci., 9(6):1095-105 (2000).
Anderson, I. The properties of hyaluronan and its role in wound healing, Prof. Nurse., 17(4):232-5 (2001).
BD PuraMatrix Peptide Hydrogel, Catalog No. 354250, BD Biosciences, 1-16 (2004).
BD PuraMatrix Peptide Hydrogel, Product Specification Sheet, 1 page. (2004).
Bouten, C.V. et al, Substrates for cardiovascular tissue engineering, Adv. Drug Deliv. Rev., 63(4-5):221-41 (2011).
Branco, M.C. and Schneider, J.P., Self-assembling materials for therapeutic delivery, Acta. Biomaterialia, 5(3): 817-831 (2009).
Caplan, M.R. et al., Control of self-assembling oligopeptide matrix formation through systematic variation of amino acid sequence, Biomaterials, 23(1):219-27 (2002).
Caplan, M.R. et al., Self-assembly of a beta-sheet protein governed by relief of electrostatic repulsion relative to van der Waals attraction, Biomacromolecules, 1(4):627-31 (2000).
Censi, R. et al, Hydrogels for protein delivery in tissue engineering, J. Control Release, 161(2):680-692 (2012).
Chen, K. et al, A Hybrid Silk/RADA-Based Fibrous Scaffold with Triple Hierarchy for Ligament Regeneration, Tissue Eng. Part A., 18(13-14):1399-409 (2012).
Chen, P., Self-assembly of ionic-complementary peptides: a physicochemical viewpoint, Colloids and Surfaces A: Physicochemical and Engineering Aspects, 261(1-3): 3-24 (2005).
Cigognini, D. et al, Evaluation of early and late effects into the acute spinal cord injury of an injectable functionalized self-assembling scaffold, PLoS One., 6(5): e19782 (2011).
Concaro, S. et al, Effect of different materials on the proliferation and migration of articular chondrocytes, Osteoarthritis and Cartilage, 15:Supplement B, pp. B119 (2007).
Cooper et al., Testing the "critical-size" in calvarial bone defects: revisiting the concept of a critical-sized defect (CSD), Plast Reconstr Surg. 125(6): 1685-1692, 2010.
Cunha, C. et al, Emerging nanotechnology approaches in tissue engineering for peripheral nerve regeneration, Nanomedicine, 7(1):50-59 (2011).
Curley, J.L. et al, Fabrication of micropatterned hydrogels for neural culture systems using dynamic mask projection photolithography, J. Vis. Exp., 48: 2636 (2011).
Davis, M.E. et al, Custom design of the cardiac microenvironment with biomaterials, Circ Res., 97(1):8-15 (2005).
Davis, M.E. et al, Injectable self-assembling peptide nanofibers create intramyocardial microenvironments for endothelial cells, Circulation, 111(4):442-450 (2005).
Davis, M.E. et al, Local myocardial insulin-like growth factor 1 (IGF-1) delivery with biotinylated peptide nanofibers improves cell therapy for myocardial infarction, Proc. Natl. Acad. Sci. USA. ,103(21):8155-8160 (2006).
Declaration of Dr. Terence Norchi, MD, for use in proceedings against EP 1879606, 4 pages (Mar. 31, 2016).
Declaration of Rutledge Ellis-Behnke for WO 2006/116524, 6 pages, Aug. 10, 2015.
Dutta, R.C. and Dutta, A.K., Comprehension of ECM-Cell dynamics: A prerequisite for tissue regeneration, Biotechnol. Adv., 28(6):764-769 (2010).

(56) References Cited

OTHER PUBLICATIONS

Dégano, I.R. et al, The effect of self-assembling peptide nanofiber scaffolds on mouse embryonic fibroblast implantation and proliferation, Biomaterials, 30(6):1156-65 (2009).
Eisenbud, D. et al, Hydrogel Wound Dressings: Where Do We Stand in 2003?, Ostomy Wound Manage, 49(10): 52-57 (2003).
Ellis-Behnke, R. et al, Crystal clear surgery with self-assembling molecules that act as a barrier in the brain and intestine, Abstracts / Nanomedicine: Nanotechnology, Biology, and Medicine, 1:269-270 (2005).
Ellis-Behnke, R., At the nanoscale: nanohemostat, a new class of hemostatic agent, WIREs Nanomedicine and Nanobiotechnology, 3: 70-78 (2011).
Ellis-Behnke, R.G. et al, Nano neuro knitting: peptide nanofiber scaffold for brain repair and axon regeneration with functional return of vision, Proc. Natl. Acad. Sci. USA, 103(13):5054-5059 (2006).
Ellis-Behnke, R.G. et al., Nano hemostat solution: immediate hemostasis at the nanoscale, Nanomedicine, 2(4):207-15 (2006).
English Translation of Office Action for JP2007-520521 (dated Aug. 24, 2011).
Experimental Report conducted at Arch Therapeutics, $(EAKA)_4$ Acetate, 6 pages, (Jul. 2014).
Experimental Report conducted by Ellis-Behnke, 1. Kidneys (rats).
Extended European Search Report for EP 13813181.8, 7 pages (dated Apr. 12, 2016).
Extended European Search Report for EP05770153.4, 7 pages (dated Apr. 7, 2011).
Garreta, E. et al, Osteogenic differentiation of mouse embryonic stem cells and mouse embryonic fibroblasts in a three-dimensional self-assembling peptide scaffold, Tissue Eng., 12(8):2215-27 (2006).
Gelain, F. et al, Slow and sustained release of active cytokines from self-assembling peptide scaffolds, J. Control Release, 145(3):231-239 (2010).
Gelain, F. et al., Designer self-assembling peptide scaffolds for 3-d tissue cell cultures and regenerative medicine, Macromol. Biosci. 7(5):544-551 (2007).
Gervaso, F. et al, The biomaterialist's task: scaffold biomaterials and fabrication technologies, Joints 1(3): 130-137 (2013).
Giri, S. and Bader, A., Improved preclinical safety assessment using micro-BAL devices: the potential impact on human discovery and drug attrition,_Drug Discov. Today, 16(9-10):382-397 (2011).
Gonzales, A.L. et al., Integrin interactions with immobilized peptides in polyethylene glycol diacrylate hydrogels, Tissue Eng., 10(11-12):1775-86 (2004).
Guo, H.D. et al, Sustained delivery of VEGF from designer self-assembling peptides improves cardiac function after myocardial infarction,_Biochem. Biophys. Res. Commun., 424(1):105-111 (2012).
Guo, H.D. et al, Transplantation of marrow-derived cardiac stem cells carried in designer self-assembling peptide nanofibers improves cardiac function after myocardial infarction, Biochem. Biophys. Res. Commun., 399(1):42-48 (2010).
Guo, J. et al, Reknitting the injured spinal cord by self-assembling peptide nanofiber scaffold, Nanomedicine, 3(4):311-321 (2007).
Gurski, L.A. et al, 3D Matrices for Anti-Cancer Drug Testing and Development, Oncology, Issues Jan./Feb. 2010: 20-25.
Hartgerink, J.D. et al., Peptide-amphiphile nanofibers: a versatile scaffold for the preparation of self-assembling materials, Proc. Natl. Acad. Sci. U S A., 99(8):5133-8 (2002).
Hemmrich, K. et al., Implantation of preadipocyte-loaded hyaluronic acid-based scaffolds into nude mice to evaluate potential for soft tissue engineering, Biomaterials, 26(34):7025-37 (2005).
Henriksson, H. et al, Investigation of different cell types and gel carriers for cell-based intervertebral disc therapy, in vitro and in vivo studies, J. Tissue Eng. Regen. Med., doi: 10.1002/term.480 (2011).
Henriksson, H.B. et al, Transplantation of human mesenchymal stems cells into intervertebral discs in a senogeneic porcine model, Spine (Phila Pa 1976), 34(2):141-148 (2009).

Hilton, J. R. et al, Wound Dressings in Diabetic Foot Disease, Clinical Infectious Diseases, 39: S100-3 (2004).
Hollinger, J.O. and Kleinschmidt, J.C., "The critical size defect as an experimental model to test bone repair materials," J. Craniofac Surg 1990(1): 60-68.
Holmes, T.C. et al., Extensive neurite outgrowth and active synapse formation on self-assembling peptide scaffolds, Proc. Natl. Acad. Sci. U S A., 97(12):6728-33 (2000).
Hsieh, P.C. et al, Controlled delivery of PDGF-BB for myocardial protection using injectable self-assembling peptide nanofibers, J. Clin. Invest.,116(1):237-248 (2006).
Hsieh, P.C.H. et al, Local controlled intramyocardial delivery of platelet-derived growth factor improves postinfarction ventricular function without pulmonary toxicity, Circulation, 114(7):637-644 (2006).
Huang, A.H. et al, Mechanics and mechanobiology of mesenchymal stem cell-based engineered cartilage, J. Biomech., 43(1):128-136 (2010).
International Search Report for PCT/US2005/024198, 3 pages (dated Feb. 23, 2006).
International Search Report for PCT/US2007/025271, 6 pages (dated Sep. 4, 2008).
Kates, Declaration of Steven Kates, Ph.D., Re: Japanese Patent Application No. 2008-509090 ("Third Party Declaration") (2012).
Kim, J.H. et al, The enhancement of mature vessel formation and cardiac function in infarcted hearts using dual growth factor delivery with self-assembling peptides, Biomaterials, 32(26):6080-6088 (2011).
Kisiday, J. et al, Self-assembling peptide hydrogel fosters chondrocyte extracellular matrix production and cell division: implications for cartilage tissue repair, Proc. Natl. Acad. Sci. USA, 99(15):9996-10001 (2002).
Kohgo, T. et al, Poster 110: Bone Regeneration for Dental Implants Using Tissue-Engineered Bone With Self-Assembling Peptide Nanofiber 3-Dimensional (3D) Scaffolds, Journal of Oral and Maxillofacial Surgery, 65(9): Supplement, p. 43.e63 (2007).
Komatsu, S. et al, The Neutral Self-Assembling Peptide Hydrogel SPG-178 as a Topical Hemostatic Agent, PLoS ONE, 9(7): e102778 (2014).
Kopecek, J. and Yang, J., Peptide-directed self-assembly of hydrogels, Acta Biomaterialia, 5(3): 805-816 (2009).
Kumada, Y. and Zhang, S., Significant type I and type III collagen production from human periodontal ligament fibroblasts in 3D peptide scaffolds without extra growth factors, PLoS One, 5(4):e10305 (2010).
Kyle, S. et al., Production of self-assembling biomaterials for tissue engineering, Trends Biotechnol., 27(7):423-33 (2009).
Lampe, K.J. and Heilshorn, S.C., Building stem cell niches from the molecule up through engineered peptide materials, Neurosci. Lett., 519(2):138-46 (2012).
Leung, G.K. et al, Peptide nanofiber scaffold for brain tissue reconstruction, Methods Enzymol., 508:177-190 (2012).
Li, X. et al, Engineering neural stem cell fates with hydrogel design for central nervous system regeneration, Progress in Polymer Science, 37(8):1105-1129 (2012).
Liedmann, A. et al, Cultivation of human neural progenitor cells in a 3-dimensional self-assembling peptide hydrogel, J. Vis. Exp., (59):e3830 (2012).
Liu, J. et al, Controlled release of paclitaxel from a self-assembling peptide hydrogel formed in situ and antitumor study in vitro, Int. J. Nanomedicine, 6:2143-53 (2011).
Liu, W-M. et al., Diversification of Microfluidic Chip for Applications in Cell-Based Bioanalysis, Chinese Journal of Analytical Chemistry, 40(1): 24-31 (2012).
Loo, Y. et al., From short peptides to nanofibers to macromolecular assemblies in biomedicine, Biotechnol. Adv., 30(3):593-603 (2012).
Luo, Z. et al, Fabrication of self-assembling d-form peptide nanofiber scaffold d-EAK16 for rapid hemostasis, Biomaterials, 32(8):2013-20 (2011).
Maher, S.A. et al, A nano-fibrous cell-seeded hydrogel promotes integration in a cartilage gap model, J. Tissue Eng. Regen. Med., 4(1):25-29 (2010).

(56) References Cited

OTHER PUBLICATIONS

Marston, W.A. et al., Initial report of the use of an injectable porcine collagen-derived matrix to stimulate healing of diabetic foot wounds in humans, Wound Repair Regen., 13(3):243-7 (2005).

Masuhara, H. et al, Novel infectious agent-free hemostatic material (TDM-621) in cardiovascular surgery, Ann. Thorac. Cardiovasc. Surg. Methods Enzymol., 18(5):444-451 (2012).

McGrath, A.M. et al, BD © PuraMatrix® peptide hydrogel seeded with Schwann cells for peripheral nerve regeneration, Brain Res. Bull., 83(5):207-213 (2010).

Meng, H. et al, Peripferal Nerve Regeneration in Response to Synthesized Nanofiber Scaffold Hydrogel, Life Science Journal, 9(1): 42-46 (2012).

Misawa, H. et al, PuraMatrix facilitates bone regeneration in bone defects of calvaria in mice, Cell Transplant, 15(10):903-910 (2006).

Mooney, M.P. and Siegel, M.I., Animal models for bone tissue engineering of critical-sized defects (CSDs), bone pathologies, and orthopedic disease states, In: Hollinger, JO.; Einhorn, TA.; Doll, BA.; Sfeir, C.,editors. Bone Tissue Engineering. Boca Raton, FL: C.R.C. Press, pp. 217-244 (2005).

Nakahara, H. et al, Bone repair using a hybrid scaffold of self-assembling peptide PuraMatrix and polyetheretherketone cage in rats, Cell Transplant, 19(6):791-797 (2010).

Narmoneva, D.A. et al, Endothelial cells promote cardiac myocyte survival and spatial reorganization: implications for cardiac regeneration, Circulation, 110(8):962-968 (2004).

Narmoneva, D.A. et al., Self-assembling short oligopeptides and the promotion of angiogenesis, Biomaterials, 26(23):4837-46 (2005).

Nichol, J.W. et al, Co-culture induces alignment in engineered cardiac constructs via MMP-2 expression, Biochem. Biophys. Res. Commun., 373(3):360-365 (2008).

Nishimura, A. et al, Controlled release of insulin from self-assembling nanofiber hydrogel, PuraMatrixe®: application for the subcutaneous injection in rats, Eur. J. Pharm. Sci., 45(1-2):1-7 (2012).

Ortinau, S. et al, Effect of 3D-scaffold formation on differentiation and survival in human neural progenitor cells, Biomed. Eng. Online, 9(1):70 (2010).

Osterman, D.G. and Kaiser, E.T., Design and characterization of peptides with amphiphilic beta-strand structures, J. Cell Biochem., 29(2):57-72 (1985).

Patterson, J. et al., Biomimetic materials in tissue engineering, Materialstoday, 13(1-2): 14-22 (2010).

Saiga, K. et al, Combined use of bFGF and GDF-5 enhances the healing of medial collateral ligament injury, Biochem. Biophys. Res. Commun., 402(2):329-334 (2010).

Sanborn, T.J. et al., A Thermally Triggered, Enzymatically Cross-linked PEG-Peptide Hydrogel for Biomaterial Applications, Presented at 2001 Annual Meeting, Americal Institute of Chemical Engineers, Reno, NV, Nov. 4-9, 2001.

Scalfani, A.P. and Romo III., T., Injectable fillers for facial soft tissue enhancement, Facial Plast. Surg., 16(1):29-34 (2000).

Segers, V.F. and Lee, R.T., Local delivery of proteins and the use of self-assembling peptides, Drug Discov. Today, 12(13-14):561-8 (2007).

Segers, V.F.M. and Lee, R.T., Stem-cell therapy for cardiac disease, Nature 451, 937-942 (2008).

Segers, V.F.M. et al, Local delivery of protease-resistant stromal cell derived factor-1 for stem cell recruitment after myocardial infarction, Circulation, 116(15):1683-1692 (2007).

Semino, C.E. et al., Entrapment of migrating hippocampal neural cells in three-dimensional peptide nanofiber scaffold, Tissue Eng., 10(3-4):643-55 (2004).

Semino, C.E., Self-assembling peptides: from bio-inspired materials to bone regeneration, J. Dent Res., 87(7):606-616 (2008).

Serban, M.A. et al, Effects of extracellular matrix analogues on primary human fibroblast behavior, Acta Biomater., 4(1):67-75 (2008).

Shirai, K. et al, Multipotency of clonal cells derived from swine periodontal ligament and differential regulation by fibroblast growth factor and bone morphogenetic protein, J. Periodontal Res., 44(2):238-247 (2009).

Shivachar, A.C., Isolation and Culturing of Glial, Neuronal and Neural Stem Cell Types Encapsulated in Biodegradable Peptide Hydrogel, Topics in Tissue Engineering, vol. 4. Eds. N Ashammakhi, R Reis, & F Chiellini © 2008.

Sluzky, V. et al., Kinetics of insulin aggregation in aqueous solutions upon agitation in the presence of hydrophobic surfaces, Proc, Natl, Acad, Sci, U S A., 88(21):9377-81 (1991).

Song, H. et al, Hemostatic efficacy of biological self-assembling peptide nanofibers in a rat kidney model, Macromol Biosci., 10(1):33-39 (2010).

Spencer, N. J. et al, Peptide- and collagen-based hydrogel substrates for in vitro culture of chick cochleae, Biomaterials, 29(8):1028-1042 (2008).

Stiuso, P. et al., The self-association of protein SV-IV and its possible functional implications, Eur. J. Biochem., 266(3):1029-35 (1999).

Sur, S. et al, A hybrid nanofiber matrix to control the survival and maturation of brain neurons, Biomaterials, 33(2):545-55 (2012).

Takei, J., 3-Dimensional Cell Culture Scaffold for Everyone: Drug Screening, Tissue Engineering and Cancer Biology, AATEX, 11(3): 170-176 (2006).

Third Part Observation for EP 05770153.4, with exhibits, 71 pages (Aug. 25, 2014).

Third Party Observation for JP 2008-509090, 43 pages, references in English (Aug. 10, 2011).

Thonhoff, J.R. et al, Compatibility of human fetal neural stem cells with hydrogel biomaterials in vitro, Brain Res., 1187:42-51 (2008).

Tokunaga, M. et al, Implantation of cardiac progenitor cells using self-assembling peptide improves cardiac function after myocardial infarction, J. Mol. Cell. Cardiol., 49(6):972-983 (2010).

Tokunou, T. et al, Engineering insulin-like growth factor-1 for local delivery, FASEB J., 22(6):1886-1893 (2008).

Tortora, G. J., Principles of Human Anatomy, Fifth Edition, Chapter 4: The Integumentary System, 98-100 (1989).

Uemura, M. et al, Matrigel supports survival and neuronal differentiation of grafted embryonic stem cell-derived neural precursor cells, J. Neurosci. Res., 88(3):542-551 (2010).

Van Putten, S.M. et al, The downmodulation of the foreign body reaction by cytomegalovirus encoded interleukin-10, Biomaterials, 30(5):730-735 (2008).

Wang, Q.G. et al, The composition of hydrogels for cartilage tissue engineering can influence glycosaminoglycan profile, Eur. Cell Mater, 19:86-95 (2010).

Wang. T. et al, Molecular Mechanisms of RAD16-1 Peptide on Fast Stop Bleeding in Rat Models, Int. J. Mol. Sci., 13: 15279-15290 (2012).

Written Opinion for PCT/US2005/024198, 4 pages (dated Feb. 23, 2006).

Yamaoka, H. et al, Cartilage tissue engineering using human auricular chondrocytes embedded in different hydrogel materials, J. Biomed. Mater Res. A., 78(1):1-11 (2006).

Ye, Z. et al, Temperature and pH effects on biophysical and morphological properties of self-assembling peptide RADA16-I., J. Pept. Sci.,14(2):152-162 (2008).

Yla-Outinen, L. et al, Three-dimensional growth matrix for human embryonic stem cell-derived neuronal cells, J. Tissue Eng. Regen. Med., doi: 10.1002/term.1512 (2012).

Yoshimi, R. et al, Self-assembling peptide nanofiber scaffolds, platelet-rich plasma, and mesenchymal stem cells for injectable bone regeneration with tissue engineering, J. Craniofac. Surg., 20(5):1523-1530 (2009).

Yu, Y.C. et al., Construction of biologically active protein molecular architecture using self-assembling peptide-amphiphiles, Methods Enzymol., 289:571-87 (1997).

Zarzhitsky, S. and Rapaport, H., The interactions between doxorubicin and amphiphilic and acidic β-sheet peptides towards drug delivery hydrogels, J. Colloid Interface Sci. 360(2):525-531 (2011).

Zhang et al., Building from the Bottom Up, Materials Today, Review Feature, 20-27 (2003).

(56) References Cited

OTHER PUBLICATIONS

Zhang et al., Emerging Biological Materials Through Molecular Self-Assembly, Biotechnology Advances, 20: 321-339 (2002).
Zhang, S. et al, PuraMatrix: Self-Assembling Peptide Nanofiber Scaffolds, Scaffolding in Tissue Engineering, Chapter 15, 217-238 (1992).
Zhang, S. et al, Self-assembling peptides in biology, materials science and engineering, Peptide Science—Present and Future, 737-744 (1999).
Zhang, S. et al, Self-complementary oligopeptide matrices support mammalian cell attachment, Biomaterials, 16(18): 1385-1393 (1995).
Zhang, S., Hydrogels: Wet or let die, Nat. Mater., 3(1):7-8 (2004).
Zhao, X. et al., Recent development of peptide self-assembly, Progress in Natural Science 18, 6(10):653-660 (2008).
[No Author Listed] Fluid. Iwanami Rikagaku Dictionary, 3rd edition Incremental version, 2nd Print, Oct. 20, 1981, p. 1430, Partial English Translation, 1 Page.
Akers, M. J., Chapter 26: Parenteral Preparations, Remington: Essentials of Pharmaceutics, Edited by Linda Felton, Pharmaceutical Press, p. 497 (2012).
Arista™ Information Sheet, Medafor, Inc., 6 pages (2006).
Arosio, P. et al, End-to-end self-assembly of RADA 16-I nanofibrils in aqueous solutions, Biophys. J., 102(7): 1617-26 (2012).
Author Not Known, Medical Devices: Guidance Document, Borderline products, drug-delivery products and medical devices incorporating, as an integral part, an ancillary medicinal substance or an ancillary human blood derivative, European Commission, DG Enterprise and Industry, Directorate F, Unit F3 "Cosmetics and medical devices", 22 pages (Dec. 3, 2009) <http://ec.europa.eu/health/medical-devices/files/meddev/2_1_3_rev_3-12_2009_en.pdf> [last accessed on May 4, 2015].
Author Unknown, AORNs Recommended Practices for Maintaining a Sterile Field is Up for Review and Public Comment Through Mar. 25, 2005, retrieved from <<https://www.infectioncontroltoday.com/guidelines/aorns-recommended-practices-maintaining-sterile-field-review-and-public-comment-through>>, accessed on Dec. 19, 2018 (23 pages).
Author Unknown, ISO 13485, Wikipedia, retrieved from <<https://en.wikipedia.org/w/index.php?title=IS0 13485&oldid=694123721>>. Accessed on Dec. 2, 2016.
Author Unknown, Medical Device, Wikipedia, retrieved from <<https://en.wikipedia.org/w/index.php?title=medical_device&oldid=699710004>>, retrieved on Dec. 2, 2016.
Basford, P.J., et al., Endoscopic resection of sporadic duodenal adenomas: comparison of endoscopic mucosal resection (EMR) with hybrid endoscopic submucosal dissection (ESD) techniques and the risks of late delayed bleeding, Surg. Endosc., 28: 1594-1600 (2014).
Beam, J., Wound Cleansing: Water or Saline?, Journal of Athletic Training, 41(2): 196-197 (2006).
Becton, Dickinson and Company, Positively Unique: BD PosiFlush™ Pre-Filled Syringes, Brochure, 6 pages (Jun. 2010).
Boyle, A. L., Applications of de novo designed peptides, Peptide Applications in Biomedicine, Biotechnology and Bioengineering, 51-86 (2017).
Cai, L. et al, Injectable Hydrogels with In Situ Double Network Formation Enhance Retention of Transplanted Stem Cells, Adv. Funct. Mater., 1-8 (2015).
Chambers, J. et al, Memorandum regarding Nucleic Acid and Peptide Claim Interpretation: "A" and "The," USPTO, 2 pages, Dec. 29, 2005.
CoSeal® Surgical Sealant, Information Sheet, Baxter Healthcare Corporation, 8 pages (2006).
CRYOLIFE®, Life Restoring Technologies, BioGlue® Instructions for Use: Surgical Adhesive Syringe Instructions for Use, L6312. 008—(Apr. 2014), pp. 1-15, 16 pages (2014).
Cunha, C. et al., 3D culture of adult mouse neural stem cells within functionalized self-assembling peptide scaffolds, International Journal of Nanomedicine, 943-955 (2011).

CyroLife: BioGlue® Surgical Adhesive, Products & Services, Website © 2007-2012,<http://web.archive.org/web/20120226221438/http://cryolife.com/products/bioglue-surgical-adhesive>, Retrieved Sep. 1, 2017.
Dojindo catalog, -SulfoBiotics-Sodium sulfide (Na2S), retrieved from http://www.dojindo.eu.com/store/p/885-SulfoBiotics-Sodium-sulfide-Na2S.aspx, 2 pages, downloaded Apr. 25, 2018.
Driscoll, P., What are the differences and similarities between laparoscopy and endoscopy?, 1 page (2016), <https//www.quora.com/what-are-the-differences-and-similiarities-between-laparoscopy-and-endoscopy> Retrieved on Oct. 4, 2017.
Gherli, T. et al., Comparing warfarin with aspirin after biological aortic valve replacement: a prospective study, Circulation, 110(5):496-500 (2004).
Ginsberg, M., Good Medicine/Bad Medicine and the Law of Evidence: Is There a Role for Proof of Character, Propensity, or Prior Bad Conduct in Medical Negligence Litigation?, South Caroline Law Review, 63:367-402 (2011).
Hirai, K. et al, The fundamental study of Matrigel (PuraMatrix TM) for the hemostasis of bleeding from pulmonary artery and vein or the prevention of lung fistel, Gen Thorac Cardiovasc Surg, 59 (Supplement): 600 (2011).
Hwang, W. et al., Supramolecular structure of helical ribbons self-assembled from a beta-sheet peptide, The Journal of Chemical Physics, 118(1): 389-397 (2003).
Ingenito, E. P. et al, Bronchoscopic Lung Volume Reduction in Severe Emphysema, Proc. Am. Thorac Soc., 5(4): 454-460 (2008).
InjectorForce Max™, Olympus, Brochure, 3 pages (2012).
International Search Report for PCT/US2013/049327 (Fill-Finish Process for Peptide Solutions, filed Jul. 3, 2013), issued by ISA/US, 3 pages (dated Jan. 10, 2014).
Koh, R., et al. Antithrombotic drugs are risk factors for delayed postoperative bleeding after endoscopic submucosal dissection for gastric neoplasms, Gastrointest. Endosc., 78: 476-483 (2013).
Kubba, A.K. and Palmer, K. R., Role of endoscopic injection therapy in the treatment of bleeding peptic ulcer, British Journal of Surgery, 83: 461-468 (1996).
Kyle, S. et al, Recombinant self-assembling peptides as biomaterials for tissue engineering, Biomaterials, 31: 9395-9405 (2010).
Lao, W., Repair Medical Science and Tissue Engineering, Chemical Industry Press, 1st ed., pp. 91-93 (2003). [Chinese].
Lee, J. et al., Three-dimensional cell culture matrices: state of the art, Tissue Eng. Part B Rev., 14(1):61-86 (2008).
Leon, E.J. et al., Mechanical properties of a self-assembling oligopeptide matrix, J. Biomater. Sci. Polymer Edn., 9(3):297-312 (1998).
Lin, H-J. et al, A prospective, randomized trial of large-versus small-volume endoscopic injection of epinephrine for peptic ulcer bleeding, Gastrointestinal Endoscopy, 55(6): 615-619 (2002).
Louie, M. K. et al, Bovine Serum Albumin Glutaraldehyde for Completely Sutureless Laparoscopic Heminephrectomy in a Survival Porcine Model, Journal of Endourology, 24(3): 451-455 (2010).
Luo, Z. and Zhang, S., Designer nanomaterials using chiral self-assembling peptide systems and their emerging benefit for society, Chem. Soc. Rev., 41(13):4736-54 (2012).
Lépilliez, V., et al., Endoscopic resection of sporadic duodenal adenomas: an efficient technique with a substantial risk of delayed bleeding, Endoscopy, 40: 806-810 (2008).
Marini, D.M. et al., Left-Handed Helical Ribbon Intermediates in the Self-Assembly of a beta-Sheet Peptide, Nano Letters, 2(4):295-299 (2002).
Mcfadden, P. M., Minimally Invasive Thoracic Surgery, vol. 2, No. 3, Jul. 2000, pp. 137-144.
Moser, C. et al, Autologous fibrin sealant reduces the incidence of prolonged air leak and duration of the chest tube drainage after lung volume reduction surgery: a prospective randomized blinded study, Journal of Thoracic and Cardiovascular Surgery, 136(4): 843-849 (2008).
Olson, E. J., Hyperinflated Lungs: What does it mean?, A recent chest X-ray showed that I have hyperinflated lungs. What could cause this?, Mayo Clinic, Nov. 30, 2017, retrieved from <<https://

(56) References Cited

OTHER PUBLICATIONS www.mayoclinic.org/diseases-conditions/emphysema/expert-answers/hyperinflated-lungs/faq-20058169>>, 3 pages, accessed Feb. 14, 2019.

Ono, S. et al., Thienopyridine derivatives as risk factors for bleeding following high risk endoscopic treatments: Safe Treatment on Antiplatelets (STRAP) study, Endoscopy, 47: 632-637 (2015).

Paramasivam, E., Air leaks, pneumothorax, and chest drains, Continuing Education in Anesthesia, Critical Care & Pain, vol. 8 No. 6 2008.

Pioche, M. et al, A self-assembling matrix-forming gel can be easily and safely applied to prevent delayed bleeding after endoscopic resections, Endoscopy International Open, 4: E415-E419 (2016).

Reich, I. et al., Chapter 36: Tonicity, Osmoticity, Osmolality, and Osmolarity, Remington: Practice of the Science and Pharmacy, 19th edition, Mack Publishing Company, 613-621 (1995).

Sigma-Aldrich catalog, Sodium Bicarbonate, retrieved from https://www.sigmaaldrich.com/catalog/product/sigma/s5761 ?lang=en &region=US, 4 pages, downloaded on Apr. 25, 2018.

Spotnitz, W. D. and Banks, S., Hemostats, sealants and adhesives: components of the surgical toolbox, Transfusion, 48: 1502-1516 (2008).

Stark, J. and De Leval, M., Experience with fibrin seal (Tisseel) in operations for congenital heart defects, Ann. Thorac. Surg., 38(4):411-3 (1984).

Tam, J. et al., Fractional skin harvesting: autologous skin grafting without donor-site morbidity, Plastic and Reconstructive Surgery Global Open, 1(6): e47 (2013).

The University of Waterloo, Buffer Solutions, retrieved from https ://web .archive.org/web/20001213162000/http://www. science .uwaterloo .ca/-cchieh/cact/c123/buffer.htm, 6 pages, downloaded on Apr. 24, 2018.

Week 201413 Thomson Scientific, London, GB; AN 2013-U98585, XP0027 40500, Use of nigella glandulifera freyn 3 seed grass volatile oil for preparing medicine for treating chronic obstructive pulmonary disease, & CN 103 251 690 A People's Liberation Army Xinjiang Milita) Aug. 21, 2013 (Aug. 21, 2013) abstract.

Written Opinion for PCT/US2013/049327 (Fill-Finish Process for Peptide Solutions, filed Jul. 3, 2013), issued by ISA/US, 7 pages (Jan. 10, 2014).

Wu, M. et al., Self-assembling peptide nanofibrous hydrogel on immediate hemostasis and accelerative osteosis, Biomacromolecules, 16: 3112-3118 (2015).

Wu, X. et al, Functional self-assembling peptide nanofiber hydrogel for peripheral nerve regeneration, Regenerative Biomaterials, 21-30 (2016).

Yamamoto, H. et al, A novel method of endoscopic mucosal resection using sodium hyaluronate, Gastrointestinal Endoscopy, 50(2): 251-256 (1999).

Yokoi, H. et al., Dynamic reassembly of peptide RADA16 nanofiber scaffold, Proc. Natl. Acad. Sci. U S A, 102(24):8414-9 (2005).

Yoshida, M, et al., Initial clinical trial of a novel hemostat, TDM-621, in the endoscopic treatments of the gastric tumors, J. Gastroenterol Hepatol., 29: 77-79 (2014).

Zhang, S. Self-assembling peptide materials, Amino Acids, Pept. Proteins, 37:40-65 (2012).

Zhang, S., Beyond the Petri dish, Nat. Biotechnol., 22(2):151-2 (2004).

Zhang, S., Designer Self-Assembling Peptide Nanofiber Scaffolds for Study of 3-D Cell Biology and Beyond, Cancer Research, 335-362 (2008).

Zhang, S., Fabrication of novel biomaterials through molecular self-assembly, Nat. Biotechnol., 21(10):1171-8 (2003).

Zhaoyang, Y. et al., Temperature and pH effects on biophysical and morphological properties of self-assembling peptide RADA16-T, Journal of Peptide Science, 14(2):152-162 (2008).

Zhou, X-R. et al., Self-assembly of PH and calcium dual-responsive peptide-amphiphilic hydrogel, Journal of Peptide Science, 19: 737-744 (2013).

\* cited by examiner

FILL-FINISH PROCESS FOR PEPTIDE SOLUTIONS

SEQUENCE LISTING

The present specification makes reference to a Sequence Listing submitted in electronic form as an ASCII .txt file named "2004837-0032_Sequences_ST25" on Jul. 3, 2013. The .txt file was generated on Jun. 10, 2013 and is 11 KB in size.

BACKGROUND OF THE INVENTION

Purified protein and/or peptide mixtures can be administered to patients for a variety of therapeutic uses. A peptide solution prepared for application to patients must be sterilized prior to use. The purification and packaging of peptides, and biotech products in general, can be exceptionally difficult. The products are complex, may be sensitive to light, temperature, pressure, pH, radiation, mechanical disturbances and otherwise sensitive to environmental conditions. Furthermore, the products may physically change or degrade easily, even under ideal processing conditions. A suitable sterilization process for some proteins (including oligopeptides) includes filtration of a peptide solution. The filter can be sized to retain (i.e., remove from the peptide solution) particulates, microorganisms, and viruses, while the proteins are able to pass through the membrane.

Accordingly, it would be desirable to develop a method of filtering and packaging a peptide solution in a manner that does not substantially damage the peptides, yet which method still permits a suitably high process throughput (i.e., filtration rate) over time. Additionally, it would be desirable to develop a filtering method generally applicable to any protein, such that the general peptide can be filtered (e.g., sterile filtered) at an efficient rate without incurring substantial damage to/loss of the peptide.

SUMMARY OF THE INVENTION

In various embodiments, the present invention includes a method to manufacture and purify peptide solutions. In some embodiments, the methods include steps of: a first deaerating step wherein a mixture comprising peptides is deaerated by lowering the pressure, filtering the mixture through a sterilizing filter; and a second deaerating step, wherein the filtrate is deaerated by vibration and lowering the pressure.

In some embodiments, methods to manufacture and purify peptide solutions of the present invention do not include filtering the mixture through a sterilizing filter. Indeed, in some embodiments, one aspect of the invention is the recognition that certain particular peptide solutions may have characteristics that render them amenable to particular preparation methodologies that may or may not be effective for other peptide solutions. In some embodiments, methods that do not utilize filtering are desirable. Alternatively or additionally, in some embodiments, provided methods to manufacture and purify peptide solutions of the present invention include heat sterilization without filtration. In some embodiments, the present invention encompasses the recognition that certain peptide solutions that do not require filtration are amenable to manufacture and/or purification using methods that include heat sterilization and/or that do not include filtration.

In some embodiments, methods that includes a filtering step utilize a sterilizing filter that has an average pore size is less than about 0.45 µm.

In some embodiments, the first deaerating step comprises lowering the pressure of the mixture at a rate of less than about −0.1 MPa/min. In some embodiments, the first deaerating step comprises lowering the pressure by about at least −0.05 MPa. In some embodiments, the lower pressure is maintained for at least about 30 minutes.

In some embodiments, the second deaerating step comprises vibrating the mixture at 150 revolutions per minute and the eccentric distance of the vibration motion is between position numbers 6 and 8. In some embodiments, the second deaerating step comprises lowering the pressure by about at least −0.05 MPa.

In some embodiments, the method further includes mixing peptides with a solvent before the first deaerating step.

In some embodiments, utilized peptide solutions are RADA-16 (SEQ ID NO: 1) peptide solutions. In some embodiments, utilize peptide solutions are or comprise an IEIK13 (SEQ ID NO: 39) peptide solution. In some embodiments, utilized peptide solutions are solutions of a peptide that appears in Table 1. In some embodiments, utilized peptide solutions are solutions of a peptide that appears in Table 2. In some embodiments, utilized peptide solutions are solutions of two or more peptides.

In some particular embodiments, the present invention provides methods to manufacture and purify IEIK13 (SEQ ID NO:39) that lack one or more filtering steps. In some embodiments, the present invention provides methods to manufacture and purify IEIK13 (SEQ ID NO:39) that do not include any filtering steps. One feature of the invention is its recognition that, at least for certain IEIK13 (SEQ ID NO:39) solutions, such filtering may not be required for sterilization.

In some embodiments, the solvent is water. In some embodiments, the method further includes aseptically filling articles with the mixture after the second deaerating step. In some embodiments, the articles are filled at least 5 hours after the second deaerating step. In some embodiments, the articles are filled at a rate of at least about 2 articles/minute, about 3 articles/minute, about 4 articles/minute, about 5 articles/minute, about 6 articles/minute, about 7 articles/minute, about 8 articles/minute, about 9 articles/minute, about 10 articles/minute, about 11 articles/minute, about 12 articles/minute, about 13 articles/minute, about 14 articles/minute, about 15 articles/minute, about 16 articles/minute, about 17 articles/minute, about 18 articles/minute, about 19 articles/minute, or about 20 articles/minute, or a multiple thereof; in some embodiments, the articles are filled at a rate of about 100, 200, 300, 400, 500, 600, 700, 800, 900, or about 1000 or more articles/hour.

In some embodiments, a high speed filling machine (e.g., such as FLS 3000, Bosch; 1I/1F/1I1VI0CY, 8I/8F/8IS-CY or 10I/10FF/10I, (KT Manufacturing Co. Ltd.) is utilized to fill the articles; in some embodiments, the high speed filling machine is or comprises a plurality of filling nozzles (e.g., 2, 3, 4, 5, etc.). In some embodiments, the machine is arranged and constructed so that each nozzle has a capacity to fill articles at a rate of at least about 2 articles/minute, about 3 articles/minute, about 4 articles/minute, about 5 articles/minute, about 6 articles/minute, about 7 articles/minute, about 8 articles/minute, about 9 articles/minute, about 10 articles/minute, about 11 articles/minute, about 12 articles/minute, about 13 articles/minute, about 14 articles/minute, about 15 articles/minute, about 16 articles/minute, about 17 articles/minute, about 18 articles/minute, about 19 articles/minute, or about 20 articles/minute or at a rate of about 100, 200, 300, 400, 500, 600, 700, 800, 900, or about 1000 or more articles/hour; and/or the machine is arranged and constructed (e.g., in some embodiments by virtue of presence of multiple nozzles) to fill articles at a rate of at least about 1000, 2000, 3000, 4000, 5000, 6000, 7000, 8000, 9000, 10000, 11000, 12000, 13000, 14000 or at least about 15000 articles/hour. In some embodiments, provided methods utilize such a high speed filing machine at least 1%, 2%, 3%, 4%, 5%, 10%, 20%, 30%, 40%, 50%, 60%, 70%, 80%, 90% or at least 100% of its capacity.

In some embodiments, the articles are syringes, pouches, vials, tubes. In some embodiments, the method further includes packaging filled articles with gas permeable materials and a sterilization step after the filling step.

In some embodiments, gas sterilization is performed by ethylene oxide gas. In some embodiments, gas sterilization is performed by hydrogen peroxide gas.

In some embodiments, the article is performed with single packaging.

In some embodiments, the article is performed with double packaging.

In some embodiments, the filtration is performed at a pressure of about 0.1-0.6 mega pascals (MPa). In some certain embodiments, the filtration is performed at a pressure of about 0.1 MPa, about 0.2 MPa, about 0.3 MPa, about 0.4 MPa, about 0.5 MPa, or about 0.6 MPa.

In some embodiments, the filtration is performed at about ambient temperature.

In some embodiments, the filter is constructed from a material selected from the group consisting of the following: cellulose nitrate, cellulose acetate, vinyl polymers, fluorocarbons, polyethylene, ultrahigh molecular weight polyethylene, polypropylene, EVA copolymers and alpha olefins, metallocene olefinic polymers, PFA, MFA, PTFE, polycarbonates, vinyl copolymers, polyamides, nylon, polyesters, cellulose, cellulose acetate, regenerated cellulose, cellulose composites, polysulfone, polyethersulfone, polyarylsulfone, polyphenylsulfone, polyacrylonitrile, polyvinylidene fluoride (PVDF), and blends thereof.

In some embodiments, the filter is constructed from polyethersulfone.

In some embodiments, the filtering step comprises a step of filling the filter at a first pressure, then increasing the pressure to perform the filtration. In some embodiments, additional tank is placed between pressure source and filtration feed tank to keep the pressure as the pressure source to perform the filtration. In some certain embodiments, a first pressure for filing the filter is relatively weak. In some embodiments, a first pressure is below about 0.01 MPa. In some embodiments, a first pressure is about 0.05 MPa.

In some embodiments, the filter is tested for integrity. In some embodiments, the filter is tested for integrity using an using an integrity test instrument (e.g., such as INTEGRITEST® 4 System, Millipore; PALLTRONIC® AquaWIT Series Filter Integrity Test System or PALLTRONIC® Flowstar Series Integrity Test Instrument; Pall Corp.; Meissner's ACCUFLUX® Automated Filter Integrity Test Instrument, Meissner Filtration Products).

In some embodiments, the filter is washed prior to an integrity test. In some certain embodiments, the filter is washed with water prior to an integrity test. In some certain embodiments, the filter is washed with hot water and/or by high-pressure water prior to an integrity test. In some certain embodiments, the filter is washed with steam and/or by autoclaving prior to an integrity test.

In some embodiments, the scraper is used to feed almost all the solution from filtration feed tank to filter. In some embodiments, the filtration step includes the use of pigs to aide filtration. In some embodiments, the filtration step is performed in two filters operated in parallel. In some embodiments, the method further includes a cleaning step, which comprises adding steam to the filtration and deaeration equipment.

DEFINITIONS

By "complementary" is meant capable of forming ionic or hydrogen bonding interactions between hydrophilic residues from adjacent peptides in the scaffold, each hydrophilic residue in a peptide either hydrogen bonds or ionically pairs with a hydrophilic residue on an adjacent peptide or is exposed to solvent.

By "structurally compatible" is meant capable of maintaining a sufficiently constant intrapeptide distance to allow scaffold formation. In certain embodiments of the invention the variation in the intrapeptide distance is less than 4, 3, 2, or 1 angstroms. It is also contemplated that larger variations in the intrapeptide distance may not prevent scaffold formation if sufficient stabilizing forces are present. This distance may be calculated based on molecular modeling or based on a simplified procedure that has been previously reported (U.S. Pat. No. 5,670,483). In this method, the intrapeptide distance is calculated by taking the sum of the number of unbranched atoms on the side-chains of each amino acid in a pair. For example, the intrapeptide distance for a lysine-glutamic acid ionic pair is 5+4=9 atoms, and the distance for a glutamine-glutamine hydrogen bonding pair is 4+4=8 atoms. Using a conversion factor of 3 angstroms per atom, the variation in the intrapeptide distance of peptides having lysine-glutamic acid pairs and glutamine-glutamine pairs (e.g., 9 versus 8 atoms) is 3 angstroms.

The term "pure" is used to indicate the extent to which the peptides described herein are free of other chemical species, including deletion adducts of the peptide in question and peptides of differing lengths.

As used herein, a hydrogel such as a peptide hydrogel is "stable with respect to mechanical or physical agitation" if, when subjected to mechanical agitation, it substantially retains the physical properties (such as elasticity, viscosity, etc.), that characterized the hydrogel prior to physical agitation. The hydrogel need not maintain its shape or size and may fragment into smaller pieces when subjected to mechanical agitation while still being termed stable with respect to mechanical or physical agitation. The term "stable" does not have this meaning except when used with this phrase.

As used herein, the term "nanofiber" refers to a fiber having a diameter of nanoscale dimensions. Typically a nanoscale fiber has a diameter of 500 nm or less. According to certain embodiments of the invention a nanofiber has a diameter of less than 100 nm. According to certain other embodiments of the invention a nanofiber has a diameter of less than 50 nm. According to certain other embodiments of the invention a nanofiber has a diameter of less than 20 nm. According to certain other embodiments of the invention a nanofiber has a diameter of between 10 and 20 nm. According to certain other embodiments of the invention a nanofiber has a diameter of between 5 and 10 nm. According to certain other embodiments of the invention a nanofiber has a diameter of less than 5 nm.

DETAILED DESCRIPTION OF CERTAIN EMBODIMENTS OF THE INVENTION

The purification and packaging of peptides, and biotech products in general, can be exceptionally difficult. The products are complex, may be sensitive to light, temperature, pressure, pH, radiation, mechanical disturbances and otherwise sensitive to environmental conditions. Furthermore, the products may physically change or degrade easily, even under ideal processing conditions.

We have discovered a series of processes to enable sterilization and packaging of peptide mixtures, including self-assembling peptides mixtures. The provided methods do not utilize thermal, chemical and radiation methods for sterilization as they can degrade peptides. According to the present invention, filtration is a particularly useful method of sterilization of the peptide mixtures.

In one aspect, the invention encompasses the recognition that relying on a physical sterilization method poses problems based on the rheology of the peptide mixtures. For example, the viscosity of the peptides mixtures can change over time, or simply be very high, such looking like a gel. Provided techniques are particular useful in the purification of self-assembling peptides, which can pose particular difficulties. The present invention encompasses the discovery of a series of operations and operating conditions that can (a) produce a sterilized peptide mixture, (b) fill and sterilize packages (e.g., syringes) a the peptide mixture and/or (c) clean the processing equipment to current good manufacturing practices (cGMP). In some embodiments, the inventive filtration equipment utilizes a micron size filter (e.g., 0.2 micron polyethersulfone filter, though other sizes and materials of construction are applicable). In some embodiments, the provided filtration methods include "pre-coating" the filter (i.e., filling the filter with the media to completely cover the filter surface by removing air in filter housing at a lower pressure before increasing the pressure for active filtration). In some embodiments, provided filtration methods involve the use of a pipeline aide (e.g., a "pig") or some other mechanical means (e.g., scraping) to ensure that the maximum quantity of the peptide mixture passes through the filter. In some embodiments, provided filtration method are preceded by a deaerating step (e.g., deaeration by pressure reduction). In some embodiments, provided filtration methods are followed by a deaerating step (e.g., deaeration by vibration). In some embodiments, provided filtration method includes integrity test procedure of sterilizing filter after filtering. In some embodiments, sterilization of surface of syringes filled with peptide mixture include the use of germicidal gas (e.g., ethylene oxide, hydrogen peroxide) to avoid degradation of peptide solution in the syringe.

Self-Assembling Peptides

Peptide sequences appropriate for use with the invention include those reported in U.S. Pat. Nos. 5,670,483 and 5,955,343, and U.S. patent application Ser. No. 09/778,200, the contents of all of which are incorporated herein by reference. These peptide chains consist of alternating hydrophilic and hydrophobic amino acids that are capable of self-assembling to form an exceedingly stable beta-sheet macroscopic structure in the presence of electrolytes, such as monovalent cations. The peptide chains are complementary and structurally compatible. The side-chains of the peptide chains in the structure partition into two faces, a polar face with charged ionic side chains and a nonpolar face with alanines or other hydrophobic groups. These ionic side chains are self-complementary to one another in that the positively charged and negatively charged amino acid residues can form complementary ionic pairs. These peptide chains are therefore called ionic, self-complementary peptides, or Type I self-assembling peptides. If the ionic residues alternate with one positively and one negatively charged residue (−+−+−+−+), the peptide chains are described as "modulus I;" if the ionic residues alternate with two positively and two negatively charged residues (−−++−−++), the peptide chains are described as "modulus II." Exemplary peptide sequences for use with the invention include those listed in Table 1. In some embodiments, peptide sequences for use with the invention have at least 12 or 16 amino acid residues. Both D- and L-amino acids may be used to produce peptide chains. They may be mixed in the same chain, or peptide compositions may be prepared having mixtures of individual chains that themselves only include D- and L-amino acids.

TABLE 1

Representative Self Assembling Peptides

| Name | Sequence (n-->c) | Modulus | |
|---|---|---|---|
| RADA16-I | n-RADARADARADARADA-c | I | SEQ ID NO: 1 |
| RGDA16-I | n-RADARGDARADARGDA-c | I | SEQ ID NO: 2 |
| RADA8-I | n-RADARADA-c | I | SEQ ID NO: 3 |
| RAD16-II | n-RARADADARARADADA-c | II | SEQ ID NO: 4 |
| RAD8-II | n-RARADADA-c | II | SEQ ID NO: 5 |
| EAKA16-I | n-AEAKAEAKAEAKAEAK-c | I | SEQ ID NO: 6 |
| EAKA8-I | n-AEAKAEAK-c | I | SEQ ID NO: 7 |
| RAEA16-I | n-RAEARAEARAEARAEA-c | I | SEQ ID NO: 8 |
| RAEA8-I | n-RAEARAEA-c | I | SEQ ID NO: 9 |
| KADA16-I | n-KADAKADAKADAKADA-c | I | SEQ ID NO: 10 |
| KADA8-I | n-KADAKADA-c | I | SEQ ID NO: 11 |
| KLD12 | n-KLDLKLDLKLDL-c | | SEQ ID NO: 12 |
| EAH16-II | n-AEAEAHAHAEAEAHAH-c | II | SEQ ID NO: 13 |

TABLE 1-continued

Representative Self Assembling Peptides

| Name | Sequence (n-->c) | Modulus | |
|---|---|---|---|
| EAH8-II | n-AEAEAHAH-c | II | SEQ ID NO: 14 |
| EFK16-II | n-FEFEFKFKFEFEFKFK-c | II | SEQ ID NO: 15 |
| EFK8-II | n-FEFKFEFK-c | I | SEQ ID NO: 16 |
| KFE12 | n-FKFEFKFEFKFE-c | | SEQ ID NO: 17 |
| KFE8 | n-FKFEFKFE-c | | SEQ ID NO: 18 |
| KFE16 | n-FKFEFKFEFKFEFKFE-c | | SEQ ID NO: 19 |
| KFQ12 | n-FKFQFKFQFKFQ-c | | SEQ ID NO: 20 |
| KIE12 | n-IKIEIKIEIKIE-c | | SEQ ID NO: 21 |
| KVE12 | n-VKVEVKVEVKVE-c | | SEQ ID NO: 22 |
| ELK16-II | n-LELELKLKLELELKLK-c | II | SEQ ID NO: 23 |
| ELK8-II | n-LELELKLK-c | II | SEQ ID NO: 24 |
| EAK16-II | n-AEAEAKAKAEAEAKAK-c | II | SEQ ID NO: 25 |
| EAK12 | n-AEAEAEAEAKAK-c | IV/II | SEQ ID NO: 26 |
| EAK8-II | n-AEAEAKAK-c | II | SEQ ID NO: 27 |
| KAE16-IV | n-KAKAKAKAEAEAEAEA-c | IV | SEQ ID NO: 28 |
| EAK16-IV | n-AEAEAEAEAKAKAKAK-c | IV | SEQ ID NO: 29 |
| RAD16-IV | n-RARARARADADADADA-c | IV | SEQ ID NO: 30 |
| DAR16-IV | n-ADADADADARARARAR-c | IV | SEQ ID NO: 31 |
| DAR16-IV* | n-DADADADARARARARA-c | IV | SEQ ID NO: 32 |
| DAR32-IV | n-(ADADADADARARARAR)$_2$-c | IV | SEQ ID NO: 33 |
| EHK16 | n-HEHEHKHKHEHEHICHK-c | N/A | SEQ ID NO: 34 |
| EHK8-I | n-HEHEHKHK-c | N/A | SEQ ID NO: 35 |
| VE20* | n-VEVEVEVEVEVEVEVEVEVE-c | N/A | SEQ ID NO: 36 |
| RF20* | n-RFRFRFRFRFRFRFRFRFRF-c | N/A | SEQ ID NO: 37 |
| IEIK9 | n-IEIKIEIKI-c | I | SEQ ID NO: 38 |
| IEIK13 | n-IEIKIEIKIEIKI-c | I | SEQ ID NO: 39 |

N/A denotes not applicable
*These peptides form a β-sheet when incubated in a solution containing NaCl, however they have not been observed to self-assemble to form macroscopic scaffolds.

Many modulus I and II self-complementary peptide sequences, such as EAK16, KAE16, RAD16, RAE16, and KAD16, have been analyzed previously (Table 1). Modulus IV ionic self-complementary peptide sequences containing 16 amino acids, such as EAK16-IV, KAE16-IV, DAR16-IV and RAD16-IV, have also been studied. If the charged residues in these self-assembling peptide chains are substituted (i.e., the positive charged lysines are replaced by positively charged arginines and the negatively charged glutamates are replaced by negatively charged aspartates), there are essentially no significant effects on the self-assembly process. However, if the positively charged resides, lysine and arginine are replaced by negatively charged residues, aspartate and glutamate, the peptide chains can no longer undergo self-assembly to form macroscopic scaffolds; however, they can still form a beta-sheet structure in the presence of salt. Other hydrophilic residues, such as asparagine and glutamine, that form hydrogen-bonds may be incorporated into the peptide chains instead of, or in addition to, charged residues. If the alanines in the peptide chains are changed to more hydrophobic residues, such as leucine, isoleucine, phenylalanine or tyrosine, these peptide chains have a greater tendency to self-assemble and form peptide matrices with enhanced strength. Some peptides that have similar compositions and lengths as the aforementioned peptide chains form alpha-helices and random-coils rather than beta-sheets and do not form macroscopic structures. Thus, in addition to self-complementarity, other factors are likely to be important for the formation of macroscopic scaffolds, such as the chain length, the degree of intermolecular interaction, and the ability to form staggered arrays.

Other self-assembling peptide chains may be generated by changing the amino acid sequence of any self-assembling peptide chains by a single amino acid residue or by multiple amino acid residues. Additionally, the incorporation of specific cell recognition ligands, such as RGD or RAD, into the peptide scaffold may promote the proliferation of the encapsulated cells. In vivo, these ligands may also attract cells from outside a scaffold to the scaffold, where they may invade the scaffold or otherwise interact with the encapsulated cells. To increase the mechanical strength of the resulting scaffolds, cysteines may be incorporated into the peptide chains to allow the formation of disulfide bonds, or residues with aromatic rings may be incorporated and cross-linked by exposure to UV light. The in vivo half-life of the scaffolds may also be modulated by the incorporation of protease cleavage sites into the scaffold, allowing the scaffold to be enzymatically degraded. Combinations of any of the above alterations may also be made to the same peptide scaffold.

Self-assembled nanoscale structures can be formed with varying degrees of stiffness or elasticity. While not wishing to be bound by any theory, low elasticity may be an important factor in allowing cells to migrate into the scaffold and to communicate with one another once resident in the scaffold. The peptide scaffolds described herein typically have a low elastic modulus, in the range of 1-10 kPa as measured in a standard cone-plate rheometer. Such low values permit scaffold deformation as a result of cell contraction, and this deformation may provide the means for cell-cell communication. In addition, such moduli allow the scaffold to transmit physiological stresses to cells migrating therein, stimulating the cells to produce tissue that is closer in microstructure to native tissue than scar. Scaffold stiffness can be controlled by a variety of means including changes in peptide sequence, changes in peptide concentration, and changes in peptide length. Other methods for increasing stiffness can also be used, such as by attaching a biotin molecule to the amino- or carboxy-terminus of the peptide chains or between the amino- and carboxy-termini, which may then be cross-linked.

Peptide chains linked may be synthesized using standard f-moc chemistry and purified using high pressure liquid chromatography. After initial synthesis peptide chains may be preserved for storage by lyophilization. The formation of a peptide scaffold may be initiated by the addition of electrolytes as described herein. The hydrophobic residues with aromatic side chains may be cross-linked by exposure to UV irradiation. The extent of the cross-linking may be precisely controlled by the predetermined length of exposure to UV light and the predetermined peptide chain concentration. The extent of cross-linking may be determined by light scattering, gel filtration, or scanning electron microscopy using standard methods. Furthermore, the extent of cross-linking may also be examined by HPLC or mass spectrometry analysis of the scaffold after digestion with a protease, such as matrix metalloproteases. The material strength of the scaffold may be determined before and after cross-linking, as described herein.

TABLE 2

| Representative Peptide Sequences for Cross-Linking | | |
|---|---|---|
| Name | Sequence (N-->C) | |
| RGDY16 | RGDYRYDYRYDYRGDY | SEQ ID NO: 40 |
| RGDF16 | RGDFRFDFRFDFRGDF | SEQ ID NO: 41 |

TABLE 2-continued

| Representative Peptide Sequences for Cross-Linking | | |
|---|---|---|
| Name | Sequence (N-->C) | |
| RGDW16 | RGDWRWDWRWDWRGDW | SEQ ID NO: 42 |
| RADY16 | RADYRYEYRYEYRADY | SEQ ID NO: 43 |
| RADF16 | RADFRFDFRFDFRADF | SEQ ID NO: 44 |
| RADW16 | RADWRWDWRWDWRADW | SEQ ID NO: 45 |

If desired, peptide scaffolds may also be formed with a predetermined shape or volume. To form a scaffold with a desired geometry or dimension, an aqueous peptide solution is added to a pre-shaped casting mold, and the peptide chains are induced to self-assemble into a scaffold by the addition of an electrolyte, as described herein. The resulting geometry and dimensions of the macroscopic peptide scaffold are governed by the concentration and amount of peptide solution that is applied, the concentration of electrolyte used to induce assembly of the scaffold, and the dimensions of the casting apparatus.

If desired, peptide scaffolds may be characterized using various biophysical and optical instrumentation, such as circular dichroism (CD), dynamic light scattering, Fourier transform infrared (FTIR), atomic force microscopy (ATM), scanning electron microscopy (SEM), and transmission electron microscopy (TEM). For example, biophysical methods may be used to determine the degree of beta-sheet secondary structure in the peptide scaffold. Additionally, filament and pore size, fiber diameter, length, elasticity, and volume fraction may be determined using quantitative image analysis of scanning and transmission electron microscopy. The scaffolds may also be examined using several standard mechanical testing techniques to measure the extent of swelling, the effect of pH and electrolyte concentration on scaffold formation, the level of hydration under various conditions, and the tensile strength.

Aqueous solution of self-assemble peptide is viscous to gel-like, the viscosity of which varies in time. The viscosity of the peptide solution becomes higher and higher when no forces (e.g., shear) is given to the solution. It needs continuous force to keep low viscosity of self-assembling peptide solution. The nature of self-assemble peptide makes formulation more difficult than most liquid formulation. Manufacturing process should be designed for the self-assembling peptide to meet regulatory requirement for medical use and reduce the loss of product in commercial scale manufacturing, as described below.

Dissolution

Synthesized peptides are prepared (e.g., synthesized) by manufacturers and are stored after synthesis in a dried form (e.g., lyophilized). For final purification/sterilization and/or packaging dried peptides should be dissolved in a solvent (e.g., water) at a concentration suitable for the ultimate use/administration.

A dissolution step begins the fill-finish process. In the broadest embodiment, dissolution begins by mixing powdered peptides (e.g., freeze-dried or lyophilized peptides) with water. In some embodiments, the water is bacteriostatic water for injection. In some embodiments, the water is sterile, deionized and/or distilled water. The peptides are dissolved so that the concentration of peptides is between about 0.1 weight percent and about 5 weight percent (e.g., about 0.2 weight percent, about 0.3 weight percent, about 0.4 weight percent, about 0.5 weight percent, about 0.75 weight percent, about 1.0 weight percent, about 1.25 weight percent, about 1.5 weight percent, about 1.75 weight percent, about 2.0 weight percent, about 2.25 weight percent, about 2.5 weight percent, about 2.75 weight percent, and ranges there between). In some embodiments, this concentration is the concentration of the peptides in solution for the final application and/or end use. Final applications or end uses of the peptide solution may influence or determine the concentration at which the peptides are dissolved in solution. In some embodiments, the peptide solution has a concentration of peptides between about 1 weight percent and about 3 weight percent. In calculations of weight percent the moisture content of the peptide powder may be accounted for. In some embodiments, the moisture content of the peptide power is between about 1 weight percent and about 10 weight percent of the peptide powder (e.g., about 5 weight percent).

In some embodiments, peptide power is added to a premeasured amount of water. In some embodiments, peptide power is added slowly or in steps so that one addition of peptides is fully dissolved before a subsequent amount of peptide power is added. Because one objective of the fill-finish process described herein is sterilization of the peptide solution, proper care should be taken to prevent bacterial contamination. Equipment used for dissolution should be autoclaved or steamed, if possible, or sanitized by irradiation (e.g., UV radiation) if autoclaving is not suitable for a particular piece of equipment.

During dissolution, the solution is stirred. Again because of viscosity and dissolution rates, the stirring rate and time are controlled. In some embodiments, the mixer used includes an axial or radial flow impeller and/or a propeller, paddle or turbine shaped impeller. In some embodiments, the mixer is operated at a rate of not less than about 500 rpm, but is brought up to that speed slowly from a stopped speed. For example, the mixer starts at a speed of about 200 rpm as the peptide power is added. Once all of the powder is dissolved the mixer speed is increased to about 500 rpm. The rotational speed of the mixer (either for initial powder addition of for mixing of the dissolved powder) can range from about 30 rpm to about 1000 rpm (e.g., about 50 rpm, about 60 rpm, about 75 rpm, about 100 rpm, about 120 rpm, about 180 rpm, about 240 rpm, about 360 rpm, about 480 rpm about 600 rpm, about 720 rpm, about 840 rpm, about 960 rpm and ranges there between) Those of skill will appreciate that the speed of the mixer depends in large part on the volume of the mixing vessel and according to the speed of the impeller, which in turn depends on the diameter of the impeller. Where v=speed of the impeller and d=the diameter of the impeller, r=rotational speed, the speed can be calculated by $v=\pi*d*r$, and should be keep proportional as the vessel size is scaled up.

Once at this speed, mixing continues for about 30 minutes (e.g., about 30 minutes, about 40 minutes, about 45 minutes, about 60 minutes and values there between). The rate of mixer speed is maintained so that the solution is not sheered to such a degree that droplets of the solution are produced from the bulk solution and thrown against the wall of the mixing vessel. The surface of the solution should be continuous, though it does not need to be level, or planar (e.g., a vortex may develop during mixing, however, its surface should be a continuous surface).

During the stirring and dissolution samples are taken from the mixing tank and inspected to monitor the dissolution. The samples are centrifuged to remove any entrained gases. The samples are then visually inspected to ensure dissolution of the peptides, also can be examined with content of dissolved peptide by photometer. If inspection indicates undissolved powder, stirring time can be extended. If inspection indicates dissolution of the peptide powder, the solution may be passed to the next stage of the fill-finish process.

If the solution is substantially completely dissolved the next step in the fill-finish process is to deaerate (e.g., degas) the solution. Our work has shown that a solution that is substantially degassed or deaerated proceeds through filtration in a more efficient manner, with less waste and/or less frequent clogging in the filter.

First Deaeration

As used herein, deaeration is equivalent to degassing, which is a process in which a dissolved or entrained gas (e.g., air) is removed from a liquid, or its quantity in the liquid reduced. The first deaerating step is performed by any acceptable deaerating method. For example, by vacuum, centrifugation, vibration, liquid-gas membrane separation or allowing the solution to degas naturally. In some embodiments, the deaerating step is performed by vacuum (e.g., by altering the pressure on the solution) In some embodiments, applied vacuum is at least −0.01 MPa, −0.015 MPa, −0.02 MPa, −0.025 MPa, −0.03, MPa, −0.035 MPa, −0.04 MPa, −0.045 MPa, −0.05 MPa, −0.055 MPa, −0.06 MPa, −0.065 MPa, −0.07 MPa, −0.075 MPa, −0.08 MPa, −0.085 MPa, −0.09 MPa, −0.095 MPa, −0.098 MPa, −0.099 MPa, −0.1 MPa or more. In some embodiments, applied vacuum is about −0.1 MPa. Among other things, the present invention encompasses the recognition that the rate of reduction of pressure (or increase in vacuum) effects the efficacy and efficiency of the deaerating process as well as the eventual filtration process. In some embodiments, the rate of pressure reduction is not more than about −0.01 MPa/minute (e.g., about −0.005 MPa/minute, about −0.0025 MPa/minute, about −0.001 MPa/minute, and ranges there between). In some embodiments, the rate of pressure reduction is dependent upon the total volume of the solution to be deaerated.

In some embodiments, the deaeration apparatus is equipped with a deaeration chamber for temporarily holding the peptide solution and a suction apparatus for reducing the pressure in the deaeration chamber. The suction apparatus can be of any design or operation to generate a vacuum. In some embodiments, the apparatus may use the dynamic pressure of a water jet, or can be any type of vacuum pump, or the like may be used as the suction apparatus.

It is preferable that a large surface area of the peptide solution inside the deaeration chamber is in contact with the air. Thus, the shape and dimensions of the deaeration chamber can be such to maximize the peptide solution's contact surface area with the air. Further, the flow into the deaeration chamber can be such that the peptide solution circulates along the inner wall of the chamber, maximizing the contact surface area. In some embodiments, the flow of peptide solution into the chamber can be as a thin film along the inner wall of the deaeration chamber. Again, the high surface area (and surface area to volume ratio of the peptide solution) can aide in deaeration efficiency. In some embodiments, however it may be sufficient that the peptide solution is simply allowed to flow into the deaeration chamber. In some particular embodiments, high viscosity (e.g., with viscosity greater than about 15.0 pascal-second [Pa·s]) solutions are allowed to flow into the deaeration chamber.

In some embodiments, solutions are stirred during aeration. In some embodiments, solutions are stirred at a rate of approximately 50 rpm, 100 rpm, 150 rpm, 200 rpm, 250 rpm, 300 rpm, 350 rpm, 400 rpm or 500 rpm. In some embodiments, it is preferable that the peptide solution that has been heated when it is introduced into the deaeration chamber. Such heating may reduce the viscosity of the solution, improving deaeration efficiency. Caution should be taken in heating as some peptides are subject to degradation with heat and therefore heating may not be appropriate in all circumstances.

Stirring can be combined with pressure reduction to efficiently deaerate from viscous peptide mixture but fast stirring might bring babble into the mixture. To dearate from peptide mixture, the mixer is operated at a rate of not less than about 300 rpm. Self-assembling peptide mixture becomes gel-like solution during deaeration if stirring is not done at the same time. Mixing self-assembling peptide solution keeps low viscosity so that the solution is effectively deaerated.

The deaerating step lasts (i.e., the time that vacuum is maintained) for at least about 30 minutes (e.g., about 15 minutes, about 20 minutes, about 40 minutes, about 45 minutes, about 60 minutes). The ultimate length of time for deaerating is dependent on the results, e.g., that the mixture is substantially free of dissolved gas or gas bubbles. During the deaerating samples of the solution are taken and inspected for dissolved gas or bubbles. If dissolved gas or gas bubbles are still present, the degassing process is continued. If the solution is sufficiently free of dissolved gas or bubbles then the fill-finish process can continue.

Filtration

Filters suitable for use according to the disclosed method are not particularly limited and can include surface filters, for example dead-end filters (i.e., in which the fluid to be filtered perpendicularly approaches the filter surface) and cross-flow filters (i.e., in which the fluid to be filtered travels parallel to the filter surface). See, e.g., Kirk-Othmer Encyclopedia of Chemical Technology, vol. 10, pp. 788-853 ("Filtration") (4th ed., 1993). The filters also are not particularly limited with respect to their classification size (i.e., the size above which dispersed material is retained on the filter and the size below which dispersed material passes into the filtrate). Once a filter classification size is selected for a particular application (i.e., dispersed material to be retained vs. dispersed material to pass into the filtrate), the filter should be operated considering the amount of shear generated by the carrier liquid flowing through the filter relative to the shear sensitivity of the particular protein being filtered.

After the mixture is sufficiently deaerated, the filtration step proceeds. As described above, we have discovered a series of processes to enable sterilization that does not utilize thermal, chemical and radiation methods for sterilization as they can degrade peptides. According to the present invention, filtration is a particularly useful method of sterilization of the peptide mixtures. Filtration is effective in removing residual debris and other small particles as well as sterilizing the peptide solution in a manner that does not result in degradation of the peptides. Filters retain contaminants using two major types of interactions between filters and contaminant particles. Particles are retained due to their size, and may also be retained due to adsorption to the filter material. Molecular and/or electrical forces between the particles and the filter material attract and retain these entities within the filter.

Generally, the pores of the filter are sized to remove at least a portion of contaminants contained in the peptide solution, retaining the removed dispersed contaminants on the upstream side of the filter (e.g., the inlet side) yielding a filtrate substantially free of contaminants. Specifically the filtrate should not contain contaminants in an amount that would adversely affect the use of the purified peptide solution. For examples when the dispersed contaminants include micro-organisms, the filter should be able to remove at least 99.9999% of micro-organisms that originally exists in the solution, that is the sterility assurance level (SAL: $10^{-6}$) for medical use.

The filter is generally available in various sizes (i.e., filter surface area, for example ranging from about 0.001 $m^2$ to about 10 $m^2$) and configurations (e.g., filter discs, filter cartridges). The materials of construction of the filter are selected to be compatible with the peptide mixture (e.g., prevent adherences or excessive friction with the solution). The porous membrane can be formed from materials such as cellulose nitrate, cellulose acetate, vinyl polymers, fluorocarbons, olefins such as polyethylene including ultrahigh molecular weight polyethylene, polypropylene, EVA copolymers and alpha olefins, metallocene olefinic polymers, PFA, MFA, PTFE, polycarbonates, vinyl copolymers such as PVC, polyamides such as nylon, polyesters, cellulose, cellulose acetate, regenerated cellulose, cellulose composites, polysulfone, polyethersulfone, polyarylsulfone, polyphenylsulfone, polyacrylonitrile, polyvinylidene fluoride (PVDF), and blends thereof. Depending on the mixture, the filter may be hydrophilic or hydrophobic. Preferred filters are hydrophilic and are low in protein/peptide binding.

The filtration step is, in some embodiments, performed by filtering through a filter with a specific pore size (e.g., about 0.2 micrometers). The porous membrane includes pores generally having a highly uniform size that is selected depending on the size of the dispersed contaminant to be removed from the liquid mixture. For example, in sterile filtration operations intended to remove microorganisms (while allowing the protein to pass through the filter membrane into the filtrate), the pores preferably have a size in a range of about 0.1 micrometers to about 0.5 micrometers. In some embodiments, the pore size is about 0.15 micrometers, about 0.1 micrometers. Suitable filtration systems can also include a primary filter with a pore size of, e.g., 0.2 micrometers, as well as a coarser prefilter to improve throughput and limit accumulation within the finer filter. The coarser prefilter can have a pore size in the range of about 0.4 micrometers to about 10 micrometers. (e.g., about 0.4 micrometers, about 0.45 micrometers, about 0.5 micrometers, about 0.6 micrometers, about 0.7 micrometers, about 0.8 micrometers, about 1.0 micrometers, about 1.5 micrometers, about 100.0 micrometers). Pre-filter system needs two or more filters so that peptide mixture may be much lost in the pre-filter(s). In addition, tandem pre-filtering system causes to lower the pressure in sterilizing filter, where the initial high pressure is lowered by pre-filter. Highly viscous peptide mixture, such as self-assembling peptide, requires high pressure (0.5 or more mega pascals (MPa)) for filtration, so tandem connection of pre-filter and sterilizing filter is not suitable to manufacturing process of viscous self-assembling peptides.

In various embodiments, filtration according to the present invention is performed at a pressure within a range of about 0.3-0.7, inclusive, for example, about 0.30 MPa, 0.31 MPa, 0.32 MPa, 0.33 MPa, 0.34 MPa, 0.35 MPa, 0.36 MPa, 0.37 MPa, 0.38 MPa, 0.39 MPa, 0.40 MPa, 0.41 MPa, 0.42 MPa, 0.43 MPa, 0.44 MPa, 0.45 MPa, 0.46 MPa, 0.47 MPa, 0.48 MPa, 0.49 MPa, 0.50 MPa, 0.51 MPa, 0.52 MPa, 0.53 MPa, 0.54 MPa, 0.55 MPa.; 0.56 MPa, 0.57 MPa, 0.58 MPa, 0.59 MPa, 0.60 MPa, 0.61 MPa, 0.62 MPa, 0.63 MPa, 0.64 MPa, 0.65 MPa, 0.66 MPa, 0.67 MPa, 0.68 MPa, 0.69 MPa, 0.70 MPa. In some embodiments, filtration is performed within a range of about 0.4-0.6 MPa, inclusive. In some embodiments, filtration is performed within a range of about 0.5-0.6 MPa, inclusive. In some embodiments, filtration is performed within a range of about 0.5-0.55 MPa, inclusive.

In some embodiments, filtration according to the present invention is performed at a pressure of about 0.40 MPa; in some embodiments, filtration according to the present invention is performed at a pressure of about 0.41 MPa; in some embodiments, filtration according to the present invention is performed at a pressure of about 0.42 MPa; in some embodiments, filtration according to the present invention is performed at a pressure of about 0.43 MPa; in some embodiments, filtration according to the present invention is performed at a pressure of about 0.44 MPa; in some embodiments, filtration according to the present invention is performed at a pressure of about 0.45 MPa; in some embodiments, filtration according to the present invention is performed at a pressure of about 0.46 MPa; in some embodiments, filtration according to the present invention is performed at a pressure of about 0.47 MPa; in some embodiments, filtration according to the present invention is performed at a pressure of about 0.48 MPa; in some embodiments, filtration according to the present invention is performed at a pressure of about 0.49 MPa; in some embodiments, filtration according to the present invention is performed at a pressure of about 0.50 MPa; in some embodiments, filtration according to the present invention is performed at a pressure of about 0.51 MPa; in some embodiments, filtration according to the present invention is performed at a pressure of about 0.52 MPa; in some embodiments, filtration according to the present invention is performed at a pressure of about 0.53 MPa; in some embodiments, filtration according to the present invention is performed at a pressure of about 0.54 MPa; in some embodiments, filtration according to the present invention is performed at a pressure of about 0.55 MPa; in some embodiments, filtration according to the present invention is performed at a pressure of about 0.56 MPa; in some embodiments, filtration according to the present invention is performed at a pressure of about 0.57 MPa; in some embodiments, filtration according to the present invention is performed at a pressure of about 0.58 MPa; in some embodiments, filtration according to the present invention is performed at a pressure of about 0.59 MPa; in some embodiments, filtration according to the present invention is performed at a pressure of about 0.60 MPa.

In some embodiments, pressure is monitored during filtration; in some such embodiments, adjustments may be made to maintain pressure within a desired range. In some embodiments, pressure is monitored sporadically. In some embodiments, pressure is monitored periodically. In some embodiments, pressure is monitored continuously.

In some embodiments, pressure is selected via a control on a vacuum device. In some such embodiments, actual applied pressure is not separately monitored. In some such embodiments, actual applied pressure is separately monitored.

To begin the filtration the filter is filled slowly so that gas is not entrained in the solution, (e.g., pre-coat) and all of the air forced from the filter vessel. In some embodiments, the filter is pre-filled with the peptide mixture by automatic and/or manual addition of the mixture to filter housing. Automatic addition of peptide mixture to filter housing can be done 0.05 MPa or less. In some embodiments, a pump, separate from a primary filtration pump is used to fill the filtration vessel. Additional methods can be used to generate pressure, including but not limited to gravity, compressed gas (e.g., air).

The filter, membrane or otherwise may run in a dead-end or normal flow (NF) format or a tangential flow (TFF) format. Typically, normal flow may be preferred to ensure proper sterilization and maximize efficacy of the filtration step. The choice is dependent on a number of factors, primarily the users preference or installed filtration. A TFF process and equipment may be preferred when large amounts of peptide are to be recovered as TFF is less subject to clogging or fouling than NF methods.

Temperatures during filtration can also be optionally controlled. Viscosity of the peptide solutions varies based on temperature and viscosity, in turn, affects filtration efficiency and efficacy. In some embodiments, the temperature during filtration ranges from about 0° C. and about 40° C. (e.g., about 10, 20, 30° C.). The temperature during filtration can also be optionally controlled to prevent degradation of the peptides (e.g., the temperature should not exceed 100° C.

Filter and related equipment can all be autoclavable and/or steamed. To maintain a sterile filtered solution, the solution is captured from the fiber into a sterile bag (e.g., the Millipore Mobius) or a sterile stainless tank which is connected to the outlet of the filter. Further disposable equipment (i.e., figure media, housings, etc.) may be employed to ensure sterility.

In some embodiments, to ensure substantially all of the peptide mixture is fed to the filter, a scraper is used within the filtration feed tank to remove any peptide mixture that adheres to the surface of the tank. If a scraper is not used for self-assembling peptide mixture, the mixture is left in mortar-shape in the tank because compressed peptide mixture become like a gel. Alternatively a pipeline aide may be used (e.g., a pipe pig). The peptide mixture is filter through filter at a pressure of between about 0.1 and about 1 MPa (e.g., about 0.5 MPa). The flow rate of the filtration is between about 0.5 and about 5 liters per minute. Our work has revealed that the pressure during filtration can vary with the flow rate appears to have a larger influence on the efficacy of the filtration operation.

The filter can be operated in a counter pressure mode, which results in a pressure at the outlet of the filter greater than atmospheric. To apply counter pressure to filter effectively and avoid pressure being lowered, an additional tank between pressure source and filtration feed tank can be available since the pressure of compressed gas will be lower due to inflation in airspace of the filtration feed tank. Counter pressure can be applied by any suitable source, for example, a conventional valve, flow constriction (e.g., an orifice plate), pressure regulator. A positive pressure (e.g., inlet pressure>outlet pressure) drives the peptide solution through the filter. The pressure differential, in some embodiments, may be low with suitable maximum pressure differential depending on a variety of factor include the concentration and type of peptides to be filtered. In some embodiments, the pressure differential is between about 0.01 MPa and about 1 MPa (e.g., about 0.5 MPa).

At such differential pressure, the flow rate across the filter is low enough to generate a low-shear environment that does not substantially damage the peptides in solutions. Furthermore, the low shear environment does not limit the filtration process (e.g., limit filtration efficiency or efficacy by viscosity effects, clogging or generate air pockets in the filter).

After filtration, the filter might be damaged by high pressure; in many embodiments, it will be appropriate or desirable to examine the filter by integrity test in order to assess whether damaged might have compromised quality of the sterilization. In many embodiments, the filter will be washed (e.g., by water and in particular e.g., by hot water and/or by high-pressure water) prior to an integrity test. In some embodiments, such washing removes or may remove solution that may have remained in the filter, it being appreciated that such remaining solution can sometimes affect test data. In some embodiments, a filter is washed with steam and/or by autoclaving. In some embodiments, the process utilized to wash the filter may degrade peptide remaining in the filter. For example, in some embodiments, a method (e.g., including washing with water [e.g., high pressure and/or hot water], washing with steam, autoclaving, etc.) is performed under conditions and for a time sufficient to degrade such peptide. In some embodiments, a filter is washed with water having a temperature within the range of about 70° C. to 80° C., inclusive, prior to an integrity test. In some certain embodiments, a filter is washed with water having a temperature of about 70° C. prior to an integrity test.

Second Deaeration

After filtration the peptide solution undergoes a degassing step. In this second degassing step, the now sterile mixture should be protected from any contamination, such as metallic fine particle from driving parts. Thus, the second degassing may be performed without further equipment (e.g., rotary impeller) coming in contact with the peptide solution. In some embodiments, the solution is degassed by degassing methods described above (e.g., depressurization/vacuum, vibration, settling).

In some embodiments, the mixture is degassed by vibration to lower the viscosity of peptide mixture. In some embodiments, vibration can be induced by an orbital shaker. In some embodiments, the degassing vibration movement is in more than one dimension. For example, the vessel containing sterilized peptide solution is move in the x-axis and the y-axis (and/or optionally a z-axis). This is in comparison to simple, one dimension (or single axis) vibration (i.e., shaking). In some embodiments, pressure reduction can be combined with vibration for effective deaeration.

The device vibrational motion is provided with a means for varying both the rotational speed and distance that the device moves in any particular direction. In some embodiments, the vibration frequency is about 50 cycles per minute and any particular direction. In some embodiments, the vibration frequency ranges from between about 20 cycles per minute to about 360 revolutions per minute, e.g., about 30, 40, 50, 60, 90, 100, 120, 150, 180, 210, 240, 300, 360). The circular direction of vibration is clockwise or counter-clockwise or combination of both. In some embodiments, the distance of the vibration motion is between about −20 cm and about 20 cm.

In some embodiments, the deaerating step is performed by vacuum. The pressure of the solution is reduced by at least about −0.05 MPa (e.g., −0.01 MPa, −0.015 MPa, −0.02 MPa, −0.025 MPa). We have realized that the rate of reduction of pressure (or increase in vacuum) effects the efficacy and efficiency of the deaerating process. In some embodiments, the rate of pressure reduction is not more than about −0.01 MPa/minute (e.g., about −0.005 MPa/minute, about −0.0025 MPa/minute, about −0.001 MPa/minute, and ranges there between). In some embodiments, the rate of pressure reduction is dependent upon the total volume of the solution to be deaerated.

The second Deaeration step also results in a uniformly mixed solution.

Exemplary vibration degassing equipment includes device models from Medical & Food System Co., Ltd. (JPO patent application #2010-161052; publication#2012-11364).

Filling

After the second degassing step, the peptide mixture is suitable for filling into a syringe. The syringe can be any size, e.g., 1 mL, 2 mL, 3 mL, 5 mL, 10 mL. Further, syringes can be any material of construction (e.g., glass, polyethylene, etc.). Proper filling is determined based on visual inspection, weighing. The target volume for each syringe depends on the viscosity of the solution.

Syringes are placed in a filing station and sterilized peptide solution is pumped into the syringe in the desired volumes. In some embodiments, a vacuum is then applied to the syringe after the peptide solution is introduced, but before the plunger is added. The rate of vacuum is partially dependent on the viscosity and boiling point of the peptide solution. The rate of application of vacuum can be selected so that its application does not introduce air bubbles into the peptide solution. A further aspect of filling syringes includes placing the plunger in the syringe. The plunger should be placed so that it is in contact with the peptide mixture, but without trapping air between the peptide mixture and the plunger and without the disturbing the peptide mixture to such an extent that the solution splatters within a syringe or air is incorporated in the peptide mixture.

After the syringe is filled, it is visually inspected for (a) any foreign substances or visible contaminants (b) any flaws, damage or defects to the syringe itself; and (c) any leaks. In process, inspection includes but is not limited to peptide concentration measured with UV-spectroscopic method and/or overall nitrogen content, HPLC, mass spectrogram, pH, gelation and/or viscosity, bacterial contamination and endotoxin, heavy-metal determination, residual solvent measurement. These inspection parameters can be performed repeatedly throughout the process and after the fill-finish process is complete as a final quality control. The syringe then undergoes a final assembly which may include addition of the plunger, grip and affixing a label. Syringes may be packaged into multi-unit packages (e.g., 1, 2, 3, 4, 5, etc., unit pillow or blister packs) for shipping and storage. Double packaging is also available to avoid bacterial contamination of syringe surface before use in operation room.

After packaging, the packs are sterilized by ethylene oxide gas ("EOG") or hydrogen peroxide gas sterilization. After each step, or after a batch of peptide solution has been processed, the process equipment can be cleaned, according to cGMP standards. The equipment can be cleaned in place, or disassembled and cleaned piece-by-piece. Additionally, process equipment can be sterilized by common sterilization techniques (e.g., autoclaving, irradiation, EOG, etc.).

Cleaning Equipments

Highly viscous peptide mixture is often sticking to surface of tank and pipeline. Cleaning all the equipments following cGMP is so hard for the sticky peptide mixture that manufacturers look for effective cleaning method. Since peptide is generally degraded by exposure to high temperature (e.g., 121° C.), steam or hot water is available for removing peptide mixture from the surface of tank and pipeline. Exposure to steam in clean-in-place (CIP) and autoclave of separated equipments are effective to clean the equipments. Since self-assemble peptide is also degradable by steam or autoclave, the peptide after exposure to steam or autoclave can be removable by rinsing with water. Remaining peptide on equipment can be checked by total organic carbon (TOC) measurement and cleaning efficiency can be validated by TOC, following cGMP.

EXAMPLE

Exemplary Production Validation of a Self-Assembling Peptide Solution

This Example illustrates production of a self-assembling peptide solution employing methods comprising a first deaerating step wherein a peptide solution is deaerated by lowering the pressure, filtering the mixture through a sterilizing filter, and a second deaerating step wherein the filtrate is deaerated by vibration and lowering the pressure.

Briefly, a 2.5% peptide solution was produced on a 10 L batch scale using raw peptide Ac-(RADA)$_4$-NH$_2$ (SEQ ID NO: 1) (lot#12103001). Exemplary production conditions were as follows:

Dissolution (60 minutes): 10 kg water for injection, 256.7 grams of peptide and an impeller revolution rate of 300 to 500 rpm.

A first deaeration step (60 minutes): an air vacuum of −0.099 MPa to −0.100 MPa and an impeller revolution rate of 250 rpm.

A filtration step: a 20" cartridge, 0.2 μm mesh sterile filter (Millipore Express SHF), a pre-filling pressure of 0.05 MPa, a counter filtration pressure of 0.5 MPa, a scraper diameter of 35 cm (similar to that of a dissolving tank), a pressure source tank having a capacity of 40 L, and a washing filter for an integrity test (Pure steam at 100° C.-130° C. for 30 minutes) using an integrity test instrument (INTEGRITEST® 4 System, Millipore). Peptide solution on the filter is washed prior to an integrity test (e.g., by water and in particular e.g., by hot water and/or by high-pressure water).

A second deaeration step (60 minutes): an air vacuum of 0.099 MPa to −0.100 MPa, a circular revolution rate of 100 rpm and a vibration mode distance of 10 cm.

The resulting peptide solution was employed to fill articles using a high speed filling machine. For example, syringes were filled using a 10I/10FF/10I machine (KT Manufacturing Co. Ltd.) at a rate of 1000 articles/hour utilizing two filling nozzles. The production of 1 mL (574 articles), 3 mL (1164 articles), and 5 mL (250 articles) variations were subjected to ethylene oxide gas for final sterilization.

Taken together, this example demonstrates that methods to manufacture and purify peptide solutions as described herein effectively provide peptide solutions suitably packaged for a variety of scientific and medical applications without any degradation or physical changes to the peptide mixtures.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

The invention claimed is:

1. A method comprising:
   (a) a first deaerating step wherein an aqueous liquid composition of self-assembling peptides having an amino acid sequence of RADARADARADARADA (SEQ ID NO: 1)("RADA16 peptides") present at a concentration of at least 0.5 weight % is deaerated by lowering the pressure at a rate of less than about 0.01 MPa/min,
   (b) a sterilizing step wherein the aqueous liquid composition is passed through a sterilizing filter producing an aqueous liquid filtrate, and wherein the sterilizing step is performed at a pressure of about 0.5 MPa; and
   (c) a second deaerating step, wherein the aqueous liquid filtrate is deaerated by vibration and lowering the pressure.

2. The method of claim 1, wherein the sterilizing filter has an average pore size equal or less than about 0.22 µm.

3. The method of claim 1, wherein the first deaerating step and/or the second deaerating step comprises lowering the pressure by about at least 0.095 MPa.

4. The method of claim 3, wherein the first deaerating step comprises lowering the pressure by applying a vacuum that is maintained for at least about 30 minutes.

5. The method of claim 1, wherein the second deaerating step comprises vibrating the aqueous liquid filtrate at 150 revolutions per minute and an eccentric distance of a vibration motion is between −10 cm and 10 cm.

6. The method of claim 1, further comprising a step of forming the aqueous liquid composition by mixing the self-assembling peptides with a solvent before the first deaerating step.

7. The method of claim 6, wherein the solvent is water.

8. The method of claim 1, further comprising a filling step, wherein the filling step comprising aseptically filling articles with the aqueous liquid composition after the second deaerating step.

9. The method of claim 8, wherein the articles are filled at least 5 hours after the second deaerating step.

10. The method of claim 8, wherein the articles are selected from the group consisting of syringes, pouches, vials, tubes, and combinations thereof.

11. The method of claim 8, further comprising a step of packaging the filled articles with gas permeable materials and a gas sterilization step after the filling step.

12. The method of claim 11, wherein the gas sterilization step is performed with ethylene oxide gas or hydrogen peroxide gas.

13. The method of claim 11, wherein the step of packaging the articles is performed with single or double packaging.

14. The method of claim 1, wherein the sterilizing step is performed at about ambient temperature.

15. The method of claim 1, wherein the sterilizing filter is constructed from a material selected from the group consisting of the following: cellulose nitrate, cellulose acetate, vinyl polymers, fluorocarbons, polyethylene, ultrahigh molecular weight polyethylene, polypropylene, EVA copolymers and alpha olefins, metallocene olefinic polymers, PFA, MFA, PTFE, polycarbonates, vinyl copolymers, polyamides, nylon, polyesters, cellulose, cellulose acetate, regenerated cellulose, cellulose composites, polysulfone, polyethersulfone, polyarylsulfone, polyphenylsulfone, polyacrylonitrile, polyvinylidene fluoride (PVDF), and blends thereof.

16. The method of claim 1, wherein the sterilizing filter is constructed from polyethersulfone.

17. The method of claim 1, wherein the sterilizing step comprises a step of filling the sterilizing filter at a first pressure, then increasing the pressure to pass the aqueous liquid composition through the sterilizing filter.

18. The method of claim 1, further comprising a step, prior to the step of sterilizing, of washing the sterilizing filter prior to an integrity test.

19. The method of claim 18, wherein the washing is with water.

20. The method of claim 1, wherein the sterilizing step is performed in two sterilizing filters operated in parallel.

21. The method of claim 1, further comprising a cleaning step, which comprises adding steam to filtration and deaeration equipment.

22. The method of claim 1, wherein the aqueous liquid composition is an aqueous solution.

23. The method of claim 1, wherein the aqueous liquid composition contains at least 1% weight to volume of the self-assembling peptides.

24. The method of claim 1, wherein the aqueous liquid composition is an aqueous solution, the aqueous liquid composition contains at least 1% weight to volume of the assembling peptides, and the first d.eaerating step comprises lowering the pressure of the aqueous self-liquid composition at a rate of less than about 0.01 MPa/min.

* * * * *

SEQUENCE LISTING

```
<160> NUMBER OF SEQ ID NOS: 45

<210> SEQ ID NO 1
<211> LENGTH: 16
<212> TYPE: PRT
<213> ORGANISM: Artificial Sequence
<220> FEATURE:
<223> OTHER INFORMATION: synthetic

<400> SEQUENCE: 1

Arg Ala Asp Ala Arg Ala Asp Ala Arg Ala Asp Ala Arg Ala Asp Ala
1               5                   10                  15

<210> SEQ ID NO 2
```

```
<211> LENGTH: 16
<212> TYPE: PRT
<213> ORGANISM: Artificial Sequence
<220> FEATURE:
<223> OTHER INFORMATION: synthetic

<400> SEQUENCE: 2

Arg Ala Asp Ala Arg Gly Asp Ala Arg Ala Asp Ala Arg Gly Asp Ala
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: synthetic

<400> SEQUENCE: 3

Arg Ala Asp Ala Arg Ala Asp Ala
1               5

<210> SEQ ID NO 4
<211> LENGTH: 16
<212> TYPE: PRT
<213> ORGANISM: Artificial Sequence
<220> FEATURE:
<223> OTHER INFORMATION: synthetic

<400> SEQUENCE: 4

Arg Ala Arg Ala Asp Ala Asp Ala Arg Ala Arg Ala Asp Ala Asp Ala
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: synthetic

<400> SEQUENCE: 5

Arg Ala Arg Ala Asp Ala Asp Ala
1               5

<210> SEQ ID NO 6
<211> LENGTH: 16
<212> TYPE: PRT
<213> ORGANISM: Artificial Sequence
<220> FEATURE:
<223> OTHER INFORMATION: synthetic

<400> SEQUENCE: 6

Ala Glu Ala Lys Ala Glu Ala Lys Ala Glu Ala Lys Ala Glu Ala Lys
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: synthetic

<400> SEQUENCE: 7

Ala Glu Ala Lys Ala Glu Ala Lys
1               5

<210> SEQ ID NO 8
<211> LENGTH: 16
```

```
<212> TYPE: PRT
<213> ORGANISM: Artificial Sequence
<220> FEATURE:
<223> OTHER INFORMATION: synthetic

<400> SEQUENCE: 8

Arg Ala Glu Ala Arg Ala Glu Ala Arg Ala Glu Ala Arg Ala Glu Ala
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: synthetic

<400> SEQUENCE: 9

Arg Ala Glu Ala Arg Ala Glu Ala
1               5

<210> SEQ ID NO 10
<211> LENGTH: 16
<212> TYPE: PRT
<213> ORGANISM: Artificial Sequence
<220> FEATURE:
<223> OTHER INFORMATION: synthetic

<400> SEQUENCE: 10

Lys Ala Asp Ala Lys Ala Asp Ala Lys Ala Asp Ala Lys Ala Asp Ala
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: synthetic

<400> SEQUENCE: 11

Lys Ala Asp Ala Lys Ala Asp Ala
1               5

<210> SEQ ID NO 12
<211> LENGTH: 12
<212> TYPE: PRT
<213> ORGANISM: Artificial Sequence
<220> FEATURE:
<223> OTHER INFORMATION: synthetic

<400> SEQUENCE: 12

Lys Leu Asp Leu Lys Leu Asp Leu Lys Leu Asp Leu
1               5                   10

<210> SEQ ID NO 13
<211> LENGTH: 16
<212> TYPE: PRT
<213> ORGANISM: Artificial Sequence
<220> FEATURE:
<223> OTHER INFORMATION: synthetic

<400> SEQUENCE: 13

Ala Glu Ala Glu Ala His Ala His Ala Glu Ala Glu Ala His Ala His
1               5                   10                  15

<210> SEQ ID NO 14
<211> LENGTH: 8
<212> TYPE: PRT
```

```
<213> ORGANISM: Artificial Sequence
<220> FEATURE:
<223> OTHER INFORMATION: synthetic

<400> SEQUENCE: 14

Ala Glu Ala Glu Ala His Ala His
1               5

<210> SEQ ID NO 15
<211> LENGTH: 16
<212> TYPE: PRT
<213> ORGANISM: Artificial Sequence
<220> FEATURE:
<223> OTHER INFORMATION: synthetic

<400> SEQUENCE: 15

Phe Glu Phe Glu Phe Lys Phe Lys Phe Glu Phe Glu Phe Lys Phe Lys
1               5                   10                  15

<210> SEQ ID NO 16
<211> LENGTH: 8
<212> TYPE: PRT
<213> ORGANISM: Artificial Sequence
<220> FEATURE:
<223> OTHER INFORMATION: synthetic

<400> SEQUENCE: 16

Phe Glu Phe Lys Phe Glu Phe Lys
1               5

<210> SEQ ID NO 17
<211> LENGTH: 12
<212> TYPE: PRT
<213> ORGANISM: Artificial Sequence
<220> FEATURE:
<223> OTHER INFORMATION: synthetic

<400> SEQUENCE: 17

Phe Lys Phe Glu Phe Lys Phe Glu Phe Lys Phe Glu
1               5                   10

<210> SEQ ID NO 18
<211> LENGTH: 8
<212> TYPE: PRT
<213> ORGANISM: Artificial Sequence
<220> FEATURE:
<223> OTHER INFORMATION: synthetic

<400> SEQUENCE: 18

Phe Lys Phe Glu Phe Lys Phe Glu
1               5

<210> SEQ ID NO 19
<211> LENGTH: 16
<212> TYPE: PRT
<213> ORGANISM: Artificial Sequence
<220> FEATURE:
<223> OTHER INFORMATION: synthetic

<400> SEQUENCE: 19

Phe Lys Phe Glu Phe Lys Phe Glu Phe Lys Phe Glu Phe Lys Phe Glu
1               5                   10                  15

<210> SEQ ID NO 20
<211> LENGTH: 12
<212> TYPE: PRT
<213> ORGANISM: Artificial Sequence
```

```
<220> FEATURE:
<223> OTHER INFORMATION: synthetic

<400> SEQUENCE: 20

Phe Lys Phe Gln Phe Lys Phe Gln Phe Lys Phe Gln
1               5                   10

<210> SEQ ID NO 21
<211> LENGTH: 12
<212> TYPE: PRT
<213> ORGANISM: Artificial Sequence
<220> FEATURE:
<223> OTHER INFORMATION: synthetic

<400> SEQUENCE: 21

Ile Lys Ile Glu Ile Lys Ile Glu Ile Lys Ile Glu
1               5                   10

<210> SEQ ID NO 22
<211> LENGTH: 12
<212> TYPE: PRT
<213> ORGANISM: Artificial Sequence
<220> FEATURE:
<223> OTHER INFORMATION: synthetic

<400> SEQUENCE: 22

Val Lys Val Glu Val Lys Val Glu Val Lys Val Glu
1               5                   10

<210> SEQ ID NO 23
<211> LENGTH: 16
<212> TYPE: PRT
<213> ORGANISM: Artificial Sequence
<220> FEATURE:
<223> OTHER INFORMATION: synthetic

<400> SEQUENCE: 23

Leu Glu Leu Glu Leu Lys Leu Lys Leu Glu Leu Glu Leu Lys Leu Lys
1               5                   10                  15

<210> SEQ ID NO 24
<211> LENGTH: 8
<212> TYPE: PRT
<213> ORGANISM: Artificial Sequence
<220> FEATURE:
<223> OTHER INFORMATION: synthetic

<400> SEQUENCE: 24

Leu Glu Leu Glu Leu Lys Leu Lys
1               5

<210> SEQ ID NO 25
<211> LENGTH: 16
<212> TYPE: PRT
<213> ORGANISM: Artificial Sequence
<220> FEATURE:
<223> OTHER INFORMATION: synthetic

<400> SEQUENCE: 25

Ala Glu Ala Glu Ala Lys Ala Lys Ala Glu Ala Glu Ala Lys Ala Lys
1               5                   10                  15

<210> SEQ ID NO 26
<211> LENGTH: 12
<212> TYPE: PRT
<213> ORGANISM: Artificial Sequence
<220> FEATURE:
```

<223> OTHER INFORMATION: synthetic

<400> SEQUENCE: 26

Ala Glu Ala Glu Ala Glu Ala Glu Ala Lys Ala Lys
1               5                   10

<210> SEQ ID NO 27
<211> LENGTH: 8
<212> TYPE: PRT
<213> ORGANISM: Artificial Sequence
<220> FEATURE:
<223> OTHER INFORMATION: synthetic

<400> SEQUENCE: 27

Ala Glu Ala Glu Ala Lys Ala Lys
1               5

<210> SEQ ID NO 28
<211> LENGTH: 16
<212> TYPE: PRT
<213> ORGANISM: Artificial Sequence
<220> FEATURE:
<223> OTHER INFORMATION: synthetic

<400> SEQUENCE: 28

Lys Ala Lys Ala Lys Ala Lys Ala Glu Ala Glu Ala Glu Ala Glu Ala
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: synthetic

<400> SEQUENCE: 29

Ala Glu Ala Glu Ala Glu Ala Glu Ala Lys Ala Lys Ala Lys Ala Lys
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: synthetic

<400> SEQUENCE: 30

Arg Ala Arg Ala Arg Ala Arg Ala Asp Ala Asp Ala Asp Ala Asp Ala
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: synthetic

<400> SEQUENCE: 31

Ala Asp Ala Asp Ala Asp Ala Asp Ala Arg Ala Arg Ala Arg Ala Arg
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: synthetic

```
<400> SEQUENCE: 32

Asp Ala Asp Ala Asp Ala Asp Ala Arg Ala Arg Ala Arg Ala Arg Ala
1               5                   10                  15

<210> SEQ ID NO 33
<211> LENGTH: 32
<212> TYPE: PRT
<213> ORGANISM: Artificial Sequence
<220> FEATURE:
<223> OTHER INFORMATION: synthetic

<400> SEQUENCE: 33

Ala Asp Ala Asp Ala Asp Ala Asp Ala Arg Ala Arg Ala Arg Ala Arg
1               5                   10                  15

Ala Asp Ala Asp Ala Asp Ala Asp Ala Arg Ala Arg Ala Arg Ala Arg
            20                  25                  30

<210> SEQ ID NO 34
<211> LENGTH: 17
<212> TYPE: PRT
<213> ORGANISM: Artificial Sequence
<220> FEATURE:
<223> OTHER INFORMATION: synthetic

<400> SEQUENCE: 34

His Glu His Glu His Lys His Lys His Glu His Glu His Ile Cys His
1               5                   10                  15

Lys

<210> SEQ ID NO 35
<211> LENGTH: 8
<212> TYPE: PRT
<213> ORGANISM: Artificial Sequence
<220> FEATURE:
<223> OTHER INFORMATION: synthetic

<400> SEQUENCE: 35

His Glu His Glu His Lys His Lys
1               5

<210> SEQ ID NO 36
<211> LENGTH: 20
<212> TYPE: PRT
<213> ORGANISM: Artificial Sequence
<220> FEATURE:
<223> OTHER INFORMATION: synthetic

<400> SEQUENCE: 36

Val Glu Val Glu Val Glu Val Glu Val Glu Val Glu Val Glu Val Glu
1               5                   10                  15

Val Glu Val Glu
            20

<210> SEQ ID NO 37
<211> LENGTH: 20
<212> TYPE: PRT
<213> ORGANISM: Artificial Sequence
<220> FEATURE:
<223> OTHER INFORMATION: synthetic

<400> SEQUENCE: 37

Arg Phe Arg Phe Arg Phe Arg Phe Arg Phe Arg Phe Arg Phe Arg Phe
1               5                   10                  15
```

Arg Phe Arg Phe
            20

<210> SEQ ID NO 38
<211> LENGTH: 9
<212> TYPE: PRT
<213> ORGANISM: Artificial Sequence
<220> FEATURE:
<223> OTHER INFORMATION: synthetic

<400> SEQUENCE: 38

Ile Glu Ile Lys Ile Glu Ile Lys Ile
1               5

<210> SEQ ID NO 39
<211> LENGTH: 13
<212> TYPE: PRT
<213> ORGANISM: Artificial Sequence
<220> FEATURE:
<223> OTHER INFORMATION: synthetic

<400> SEQUENCE: 39

Ile Glu Ile Lys Ile Glu Ile Lys Ile Glu Ile Lys Ile
1               5                   10

<210> SEQ ID NO 40
<211> LENGTH: 16
<212> TYPE: PRT
<213> ORGANISM: Artificial Sequence
<220> FEATURE:
<223> OTHER INFORMATION: synthetic

<400> SEQUENCE: 40

Arg Gly Asp Tyr Arg Tyr Asp Tyr Arg Tyr Asp Tyr Arg Gly Asp Tyr
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: synthetic

<400> SEQUENCE: 41

Arg Gly Asp Phe Arg Phe Asp Phe Arg Phe Asp Phe Arg Gly Asp Phe
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: synthetic

<400> SEQUENCE: 42

Arg Gly Asp Trp Arg Trp Asp Trp Arg Trp Asp Trp Arg Gly Asp Trp
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: synthetic

<400> SEQUENCE: 43

Arg Ala Asp Tyr Arg Tyr Glu Tyr Arg Tyr Glu Tyr Arg Ala Asp Tyr

```
                            -continued
1               5               10              15

<210> SEQ ID NO 44
<211> LENGTH: 16
<212> TYPE: PRT
<213> ORGANISM: Artificial Sequence
<220> FEATURE:
<223> OTHER INFORMATION: synthetic

<400> SEQUENCE: 44

Arg Ala Asp Phe Arg Phe Asp Phe Arg Phe Asp Phe Arg Ala Asp Phe
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: synthetic

<400> SEQUENCE: 45

Arg Ala Asp Trp Arg Trp Asp Trp Arg Trp Asp Trp Arg Ala Asp Trp
1               5                   10                  15
```